(12) United States Patent
Nariyuki et al.

(10) Patent No.: US 9,931,089 B2
(45) Date of Patent: Apr. 3, 2018

(54) RADIATION IRRADIATION APPARATUS

(71) Applicant: FUJIFILM Corporation, Tokyo (JP)

(72) Inventors: Fumito Nariyuki, Ashigarakami-gun (JP); Ryosuke Ogura, Ashigarakami-gun (JP); Yuzo Aoshima, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 235 days.

(21) Appl. No.: 15/084,175

(22) Filed: Mar. 29, 2016

(65) Prior Publication Data

US 2016/0287194 A1 Oct. 6, 2016

(30) Foreign Application Priority Data

Mar. 31, 2015 (JP) .................................. 2015-073253
Feb. 10, 2016 (JP) .................................. 2016-023265

(51) Int. Cl.
*A61B 6/00* (2006.01)
*A61B 6/10* (2006.01)
(52) U.S. Cl.
CPC ............ *A61B 6/4405* (2013.01); *A61B 6/107* (2013.01); *A61B 6/4411* (2013.01); *A61B 6/465* (2013.01); *A61B 6/467* (2013.01); *A61B 6/544* (2013.01); *A61B 6/588* (2013.01); *A61B 6/589* (2013.01)
(58) Field of Classification Search
CPC ..... A61B 5/0077; A61B 8/4427; A61B 6/465; A61B 6/461; A61B 8/4209; A61B 6/4405
See application file for complete search history.

(56) References Cited

U.S. PATENT DOCUMENTS

2001/0048586 A1 12/2001 Itou et al.
2009/0136000 A1 5/2009 Nishii et al.
2011/0049370 A1 3/2011 Yoshida et al.
(Continued)

FOREIGN PATENT DOCUMENTS

JP 2001-337743 A 12/2001
JP 2005-331668 A 12/2005
JP 2006-172103 A 6/2006
(Continued)

OTHER PUBLICATIONS

"AIST Data on Size of Hand of Japanese", https://www.dh.aist.go.jp/database/hand/data/list.html.
(Continued)

*Primary Examiner* — Don Wong
(74) *Attorney, Agent, or Firm* — Birch, Stewart, Kolasch & Birch, LLP

(57) ABSTRACT

A radiation irradiation apparatus includes a radiation source that irradiates, with radiation, a subject to be examined, a camera that obtains a photographic image of the subject to be examined by performing photography on the subject to be examined, a monitor that displays the photographic image, a housing that houses the radiation source, the camera and the monitor with a display direction of the photographic image directed in a second direction opposite to a first direction that is an irradiation direction of the radiation and a photography direction of the photographic image, and plural grasp units that project in directions different from the first and second directions and are attached to positions of the housing facing each other.

17 Claims, 12 Drawing Sheets

(56) References Cited

U.S. PATENT DOCUMENTS

2014/0031664 A1* 1/2014 Kang .................. A61B 6/4405
600/407

FOREIGN PATENT DOCUMENTS

| | | |
|---|---|---|
| JP | 2007-29353 A | 2/2007 |
| JP | 2008-206740 A | 9/2008 |
| JP | 2009-131323 A | 6/2009 |
| JP | 2010-119485 A | 6/2010 |
| JP | 2011-24721 A | 2/2011 |
| JP | 2011-45439 A | 3/2011 |
| JP | 2012-29889 A | 2/2012 |
| JP | 2012-110395 A | 6/2012 |

OTHER PUBLICATIONS

Japanese Office Action, dated Jan. 31, 2017, for Japanese Application No. 2016-023265, with English translation.
Japanese Office Action for Japanese Application No. 2016-023265, dated Sep. 20, 2016, with an English translation.

* cited by examiner

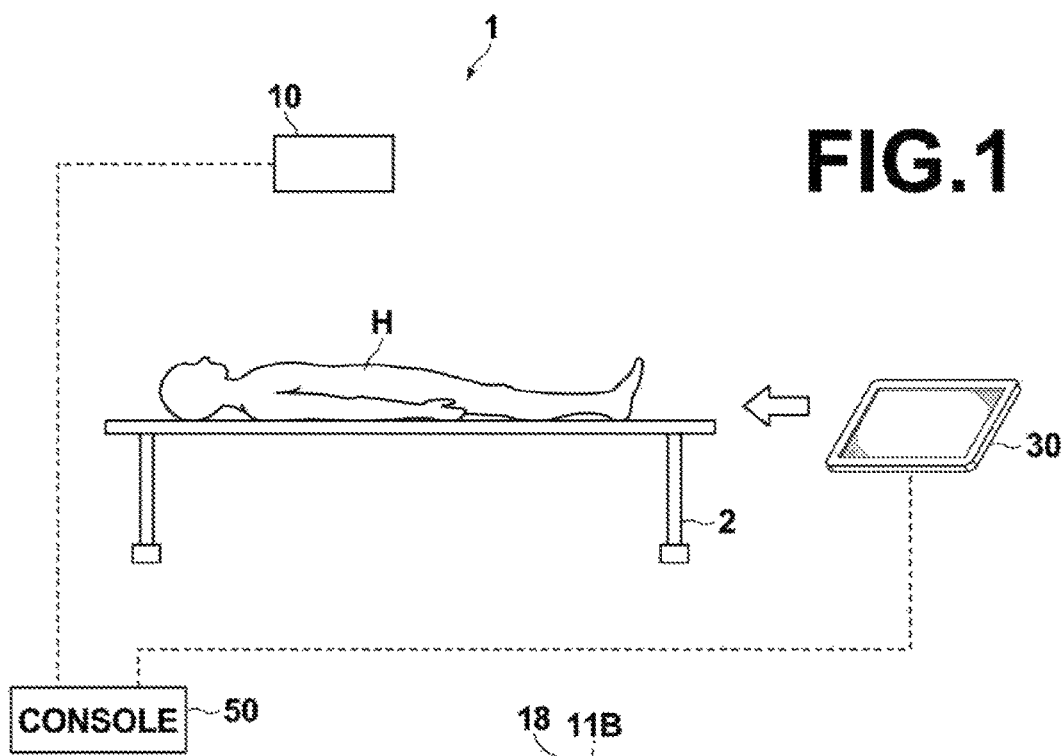
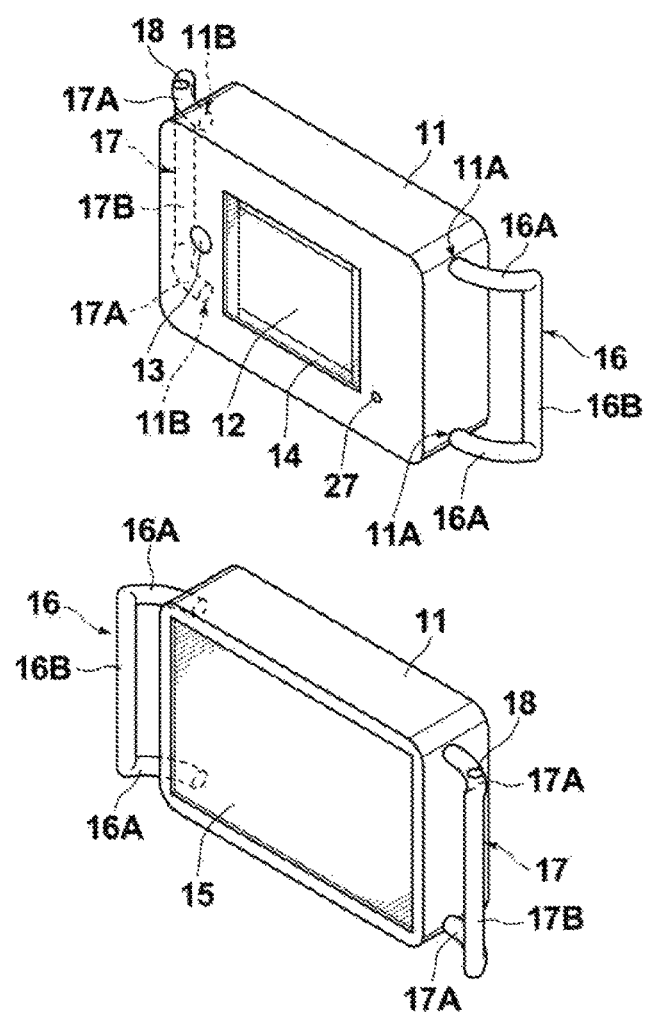

RADIATION IRRADIATION APPARATUS

CROSS-REFERENCE TO RELATED APPLICATIONS

The present application claims priority under 35 U.S.C. § 119 to Japanese Patent Applications Nos. 2015-073253, filed on Mar. 31, 2015, and 2016-023265, filed on Feb. 10, 2016. Each of the above applications is hereby expressly incorporated by reference, in its entirety, into the present application.

BACKGROUND

The present disclosure relates to a radiation irradiation apparatus that irradiates, with radiation, a subject to be examined in the case that a radiographic image of the subject to be examined is obtained.

Conventionally, various radiography apparatuses using movable radiation irradiation apparatuses were known, for example, as disclosed in Japanese Unexamined Patent Publication No. 2009-131323 (Patent Document 1), Japanese Unexamined Patent Publication No. 2007-029353 (Patent Document 2) and Japanese Unexamined Patent Publication No. 2010-119485 (Patent Document 3). Such a radiography apparatus is basically configured to irradiate, with radiation, a subject to be examined by using a doctor's-round-visit-cart-type radiation irradiation apparatus including a leg unit made travelable by wheels, a main body part that houses a battery for driving a radiation source and an electrical circuit related to drive of the radiation source and is held on the leg unit, an arm unit connected to the main body part, and the radiation source attached to the arm unit.

Further, a radiography apparatus using a portable-type radiation irradiation apparatus on which only minimum composition elements, such as a radiation source and an electrical circuit, are mounted, and which is held by hand and operated by an operator, has also been proposed (please refer to Japanese Unexamined Patent Publication No. 2012-029889 (Patent Document 4)). The weight of such a portable-type radiation irradiation apparatus has been reduced to such an extent that an operator can operate the apparatus by holding the apparatus by hand. Therefore, more flexible radiography has become possible than the aforementioned doctor's-round-visit-cart-type radiation irradiation apparatus.

In the case that a radiographic image of a subject to be examined is obtained by radiography by such a radiography apparatus, normally, a radiation detector (so-called "Flat Panel Detector"), which is irradiated with radiation that has passed through the subject to be examined and thereby records a radiographic image representing the subject to be examined, is used. As such a radiation detector, a cassette-type radiation detector, in which an image detector, a battery for driving, and a control unit of an electrical circuit related to drive or the like are housed in a housing, is known. Further, in the case that such a radiation detector is placed at a position facing a radiation irradiation apparatus with a subject to be examined therebetween, and the radiation irradiation apparatus is driven in the state, radiation that has passed through the subject to be examined irradiates the radiation detector, and a radiographic image represented by the radiation that has passed through the subject to be examined is obtained.

Further, in a radiography apparatus in which a radiation irradiation apparatus and a radiation detector are separate from each other, as described above, a technique for obtaining a photographic image representing a surface of a subject to be examined by performing photography on the subject to be examined by a camera and displaying the photographic image has been proposed to recognize an irradiation field and the like (please refer to Patent Documents 1 through 3). Further, in a radiography apparatus in which a radiation irradiation apparatus and a radiation detector are separate from each other, a difference in position tends to occur between an irradiation field of radiation and a detection range of the radiation detector. Therefore, in Patent Documents 1 through 3, a technique for performing superimposed display of a frame representing an irradiation field of radiation and a frame representing a detection area of a radiation detector on a displayed photographic image has been proposed.

SUMMARY

The radiation irradiation apparatus configured as described above is able to be easily carried even to a small space or used under conditions in which alternating current power source is not available. Such an advantage of the radiation irradiation apparatus is utilized, and the apparatus is particularly appropriately used to obtain a radiographic image of a patient transported to an emergency room in a medical institution, such as a hospital, or a patient lying on a bed in a small patient's room in the hospital.

Meanwhile, a portable-type radiation irradiation apparatus is able to be carried, but the weight of the apparatus is about 4 kilogram. Therefore, it is impossible to stably operate the apparatus without holding the apparatus by both hands. Further, in the case that an operation for outputting radiation is performed while the portable-type radiation irradiation apparatus is held by both hands, there is a risk that a hand or hands are exposed to radiation depending on a position at which the apparatus is held. In this case, an operation may be performed with gloves for preventing exposure to radiation on. However, if gloves are worn, there is a risk that input of various instructions for the apparatus becomes difficult. Further, in the case that an apparatus is held by both hands, an operation and setting of the apparatus is difficult in some cases.

In view of the foregoing circumstances, the present disclosure provides a portable-type radiation irradiation apparatus in which exposure of hands to radiation is securely prevented.

Further, the present disclosure provides the apparatus in which an operation and setting is easy.

A radiation irradiation apparatus of the present disclosure includes a radiation source that irradiates, with radiation, a subject to be examined, a photography means that obtains a photographic image of the subject to be examined by performing photography on the subject to be examined a display means that displays the photographic image, a housing that houses the radiation source, the photography means and the display means with a display direction of the photographic image directed in a second direction opposite to a first direction that is an irradiation direction of the radiation and a photography direction of the photographic image, and plural grasp units that project in directions different from the first and second directions and are attached to positions of the housing facing each other.

The "photographic image of the subject to be examined" is an image representing a surface of the subject to be examined and a surface of an object in a surrounding area of the subject to be examined within a photography range of the photography means. Here, an infrared image representing the temperature distribution of the surface of the subject to be examined and the surface of the object in the surrounding area of the subject to be examined, which has been obtained by performing photography on the subject to be examined using infrared rays, is also included as the photographic image of the subject to be examined.

The term "houses" means not only a state in which the radiation source, the photography means and the display means are provided completely in the inside of the housing, but a state in which the radiation source, the photography means and the display means are provided on the surface of the housing is also included.

In the radiation irradiation apparatus of the present disclosure, the plural grasp units may project in directions orthogonal to the first direction.

The term "orthogonal" is not necessarily limited to a direction at an angle of 90 degrees with respect to the first direction, and a case in which the angle is different from 90 degrees by about a few degrees (for example, ±5 degrees) is included.

In the radiation irradiation apparatus of the present disclosure, the display means may include a touch-panel-type input means.

In the radiation irradiation apparatus of the present disclosure, the display means may display a setting menu based on a state of touch on the input means.

The term "state of touch" means not only touching the input means, but an arbitrary state in which a state during touch is changed, such as changing a touch position while touching state is maintained or changing touch pressure at a touch position, is included. Further, touch may be performed by a finger or fingers, which may include a thumb or thumbs, of an operator, or by a touch pen or the like.

The term "setting menu" means a menu for performing setting for a radiation irradiation apparatus of the present disclosure, or performing an operation for outputting radiation.

Further, in the radiation irradiation apparatus of the present disclosure, the display means may display the setting menu at a touch position on the input means or in the vicinity of the touch position.

The term "vicinity" means an area within a distance at which the setting menu is operatable by a touching finger, fingers or the like while the grasp units are being grasped.

Further, in the radiation irradiation apparatus of the present disclosure, the setting menu may include plural commands, and the display means may arrange and display the plural commands at the touch position or in the vicinity of the touch position.

The plural commands may be linearly arranged, or arranged in arc shape or in circumference shape of an ellipse.

The term "vicinity" means an area within a distance at which the plural commands are operatable by a touching finger, fingers or the like while the grasp units are being grasped.

Further, in the radiation irradiation apparatus of the present disclosure, the input means may receive, by successive taps on a command, selection of the command successively tapped.

The "successive taps" means touching a touch-panel-type input means plural times within a certain time period.

The radiation irradiation apparatus of the present disclosure may further include a motion amount detection means that detects a motion amount of the radiation source per unit time and a radiography permission means that permits output of the radiation from the radiation source in the case that the motion amount has become less than a threshold.

In the radiation irradiation apparatus of the present disclosure, the grasp unit may include two projection units projecting from the housing and a connection unit connecting the two projection units together, and a hole may be formed by the two projection units, the connection unit and the housing.

Further, in the radiation irradiation apparatus of the present disclosure, the grasp unit may be inclined or curved toward the second direction from its projection position.

Further, in the radiation irradiation apparatus of the present disclosure, the grasp units may be detachably attached to the housing.

The radiation irradiation apparatus of the present disclosure may further include an output permission means that permits output of the radiation from the radiation source only if the grasp units are attached to the housing.

The radiation irradiation apparatus of the present disclosure may further include attachment units that can attach, to the housing, the grasp units the projection amounts of which from the housing are different.

In the radiation irradiation apparatus of the present disclosure, projection amounts of the grasp units from the housing may be changeable.

Further, in the radiation irradiation apparatus of the present disclosure, the photographic image may be an infrared image, and the display means may display the infrared image and a radiographic image of the subject to be examined.

Further, in the radiation irradiation apparatus of the present disclosure, the display means may be detachable from the housing.

Further, in the radiation irradiation apparatus of the present disclosure, the display means may display a setting menu based on the state of use.

The phrase "a setting menu based on the state of use" means a setting menu based on a state in which the radiation irradiation apparatus of the present disclosure is used. Specifically, it is possible to display a setting menu based on the state of use by changing the setting menu to different setting menus for a case in which the radiation irradiation apparatus of the present disclosure is used by being held by hand and a case in which the radiation irradiation apparatus of the present disclosure is used by being attached to a support apparatus.

A radiation irradiation apparatus of the present disclosure includes plural grasp units that project in directions different from a first direction that is an irradiation direction of radiation and a photography direction of a photographic image and a second direction that is a display direction of the photographic image and are attached to positions of a housing facing each other. Therefore, in the case that the radiation irradiation apparatus of the present disclosure is used, if the plural grasp units are held by hand, hands are not irradiated with radiation. Hence, it is possible to prevent exposure of hands to radiation. Further, in the case that a photographic image is displayed, observation of the photographic image is not disturbed by hands.

BRIEF DESCRIPTION OF THE DRAWINGS

FIG. 1 is a schematic diagram illustrating a radiography apparatus using a radiation irradiation apparatus according to an embodiment of the present disclosure;

FIG. 2 is a front-side perspective view of the radiation irradiation apparatus;

FIG. 3 is a back-side perspective view of the radiation irradiation apparatus;

DESCRIPTION OF THE PREFERRED EMBODIMENTS

Figure 4:
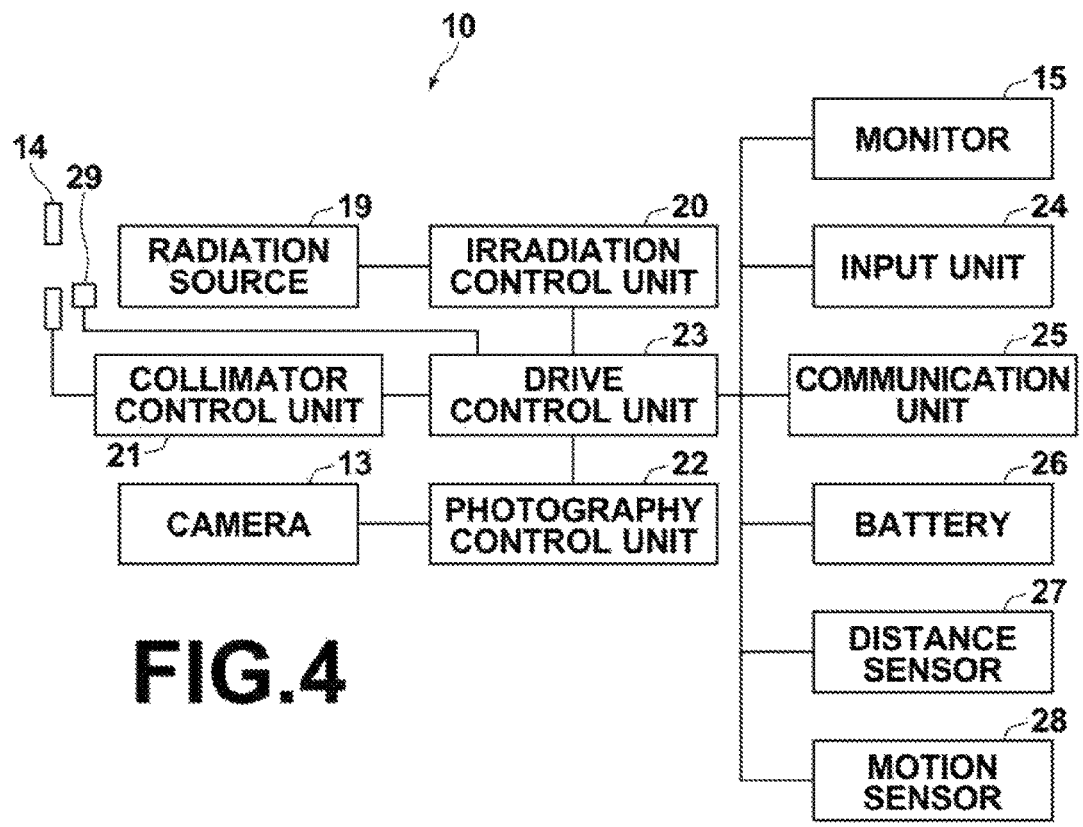
FIG. 4 is a schematic block diagram illustrating the internal configuration of the radiation irradiation apparatus.

Hereinafter, embodiments of the present disclosure will be described with reference to drawings. FIG. 1 is a schematic diagram illustrating a radiography apparatus using a radiation irradiation apparatus according to an embodiment of the present disclosure. As illustrated in FIG. 1, a radiography apparatus 1 includes a portable-type radiation irradiation apparatus 10 according to an embodiment of the present disclosure, a radiation detector 30 and a console 50. The radiation detector 30 is inserted between subject H to be examined lying on a bed 2 and the bed 2 to obtain a radiographic image of subject H to be examined, and radiation is output from the radiation irradiation apparatus 10 toward subject H to be examined, and the radiographic image of subject H to be examined is obtained by the radiation detector 30.

FIG. 2 is a front-side perspective view of a radiation irradiation apparatus. FIG. 3 is a back-side perspective view of the radiation irradiation apparatus. FIG. 4 is a schematic block diagram illustrating the internal configuration of the radiation irradiation apparatus. As illustrated in the drawings, in the radiation irradiation apparatus 10, an output window 12 through which radiation is output, a camera 13 that performs photography on a surface of subject H to be examined and a distance sensor 27 are provided on a front surface of a housing 11 in rectangular-parallelepiped shape. A collimator 14 for narrowing an irradiation range of radiation is observable from the output window 12. Further, a monitor 15 of liquid crystal or the like is provided on the back surface of the housing 11. A photographic image obtained by performing photography on the surface of subject H to be examined by the camera 13, a radiographic image of subject H to be examined, various kinds of information for setting the radiation irradiation apparatus 10 and the like are displayed on the monitor 15. The distance sensor 27 measures a distance between the radiation irradiation apparatus 10 and a target by a laser beam or ultrasonic waves.

Grasp units 16, 17 are attached to two sides of the housing 11 facing each other, respectively. The grasp unit 16 includes two projection units 16A, which project from an upper part and a lower part of a side surface of the housing 11 toward a lateral direction, and a connection unit 16B, which connects the two projection units 16A together. The grasp unit 17 includes two projection units 17A, which project from an upper part and a lower part of a side surface of the housing 11 toward a lateral direction, and a connection unit 17B, which connects the two projection units 17A together. Accordingly, the grasp units 16, 17 project in directions different from a first direction that is an irradiation direction of radiation and a photography direction of photographic image G1 and a second direction opposite to the first direction.

The projection units 16A, 17A are curved from projection positions 11A, 11B toward the back side of the housing 11, in other words, toward the display direction of a monitor, which will be described later. Here, the projection units 16A, 17A may be inclined from the projection positions 11A, 11B toward the back side of the housing 11, instead of being curved. An operator is able to move, by holding the grasp units 16, 17 by hand, the radiation irradiation apparatus 10 to a position at which photography and radiography are performable on subject H to be examined. Further, a radiography button 18 for performing radiography on subject H to be examined by outputting radiation is provided on the projection unit 17A on the upper side of the grasp unit 17, which will be held by the right hand of the operator during radiography.

A monitor 15, a radiation source 19, an irradiation control unit 20, a collimator control unit 21, a photography control unit 22, a drive control unit 23, an input unit 24, a communication unit 25, a battery 26, a distance sensor 27, a motion sensor 28 and an irradiation field lamp 29 are housed in the housing 11. Here, the irradiation control unit 20, the collimator control unit 21, the photography control unit 22, the drive control unit 23 and the communication unit 25 are configured by programs (software) that operate on a computer, specialized hardware or a combination thereof. The programs are recorded in a recording medium, such as a DVD (Digital Versatile Disc) or a CD-ROM (Compact Disk Read Only Memory), and distributed, and installed in the radiation irradiation apparatus 10 from the recording medium. Alternatively, the programs are stored in a storage device of a server computer connected to a network or a network storage in such a manner to be accessible from the outside, and downloaded in the radiation irradiation apparatus 10 based on a request, and installed.

The radiation source 19 is configured, for example, by an X-ray tube, a step-up circuit, a cooling means for cooling the X-ray tube, and the like.

The irradiation control unit 20 drives the radiation source 19, and controls the dose of radiation with which subject H to be examined is irradiated so that subject H to be examined is irradiated with radiation at an intensity based on radiography condition that has been set in advance and only for a set time period. The radiography condition is a tube voltage (kV value) and an mAs value (tube electric current×irradiation time) based on the body thickness of subject H to be examined. Here, the body thickness of subject H to be examined is obtainable by measuring an SID (Source Image Receptor Distance), which is a distance between the radiation irradiation apparatus 10 and the surface of the radiation detector 30, and an SOD (Source Object Distance), which is a distance between the radiation irradiation apparatus 10 and the surface of subject H to be examined, by the distance sensor 27, and by subtracting the SOD from the SID. Here, the operator may measure the body thickness, and input information for setting the radiography condition, including the measured body thickness, from the input unit 24 to the radiation irradiation apparatus 10. In the present embodiment, information for setting the radiography condition, such as the body thickness, is sent to the console 50, and the radiography condition is set at the console 50. Further, the set radiography condition is sent to the radiation irradiation apparatus 10. The irradiation control unit 20 controls output of radiation to subject H to be examined by using the radiography condition sent from the console 50.

The collimator control unit 21 is configured by a drive mechanism, such as a motor, an electrical circuit for controlling the drive mechanism, and the like for driving the collimator 14 and changing an irradiation field of radiation output from the radiation source 19 to subject H to be examined. The collimator control unit 21 controls drive of the collimator 14 based on an instruction from the drive control unit 23.

The photography control unit 22 obtains photographic image G1 by driving the camera 13 and performing photography on the surface of subject H to be examined. Further, the photography control unit 22 may perform image processing for improving image qualities on photographic image G1 obtained by the camera 13. Here, photographic image G1 obtained by the camera 13 is a moving image at a predetermined frame rate of 30 fps, for example.

The drive control unit 23 controls the whole drive of the radiation irradiation apparatus 10. Specifically, the drive control unit 23 performs processing for driving the radiation source 19 by instructing the irradiation control unit 20, processing for driving the collimator 14 by instructing the collimator control unit 21, processing for obtaining photographic image G1 by instructing the photography control unit 22 and driving the camera 13, processing for displaying various kinds of information including photographic image G1 on the monitor 15, processing for exchanging various kinds of information with the console 50 by instructing the communication unit 25, processing for monitoring the condition of the battery 26, processing for receiving an instruction from the input unit 24, processing for measuring a distance between the radiation irradiation apparatus 10 and a target by the distance sensor 27, processing for detecting the motion of the radiation irradiation apparatus 10 by the motion sensor 28, and the like. Here, each of the aforementioned kinds of processing is performed by an instruction from the input unit 24 or an instruction that has been sent from the console 50 and received by the communication unit 25. Here, the drive control unit 23 corresponds to the radiography permission means and the output permission means.

The input unit 24 is a touch-panel-type input unit integrated with the monitor 15. The input unit 24 receives an instruction given by an operator, and outputs information representing the instruction to the drive control unit 23. Here, the radiography button 18 is also regarded as being included in the input unit 24. In the case that the input unit 24 is a touch panel as described above, it is possible to easily perform various kinds of input for the radiation irradiation apparatus 10 while the grasp units 16, 17 are held by hand.

The communication unit 25 exchanges information by performing wireless communication with the console 50. Here, instead of wireless communication, information may be exchanged by wired communication by connecting the radiation irradiation apparatus 10 and the console 50 by cable. In the latter case, the communication unit 25 includes a connector to which a cable is connected.

The motion sensor 28 is a nine-axis motion sensor that detects acceleration on three axes, angular velocities on three axes and inclinations on three axes. The acceleration, angular velocities and inclinations detected by the motion sensor 28 are output to the drive control unit 23, as motion information, and used to control the radiation irradiation apparatus 10 during radiography, and also sent from the communication unit 25 to the console 29. Here, the motion sensor 28 corresponds to a motion amount detection means.

The irradiation field lamp 29 includes a light emitting device that outputs visible light, such as a light bulb or an LED (Light Emitting Diode), and ON/OFF of the irradiation field lamp 29 is controlled by the drive control unit 23. In the case that the irradiation field lamp 29 is turned on, an irradiation field on subject H to be examined, which will be irradiated with radiation, is illuminated with visible light.

Here, holes for inserting hands are formed between the grasp units 16, 17 and the side surfaces of the housing 11. Meanwhile, "AIST Data on Size of Hand of Japanese" (https://www.dh.aist.go.jp/database/hand/data/list.html) shows 83 mm and 95 mm, as the mean and the maximum value of hand breadths of Japanese males, respectively. Here, the hand breadth is defined as "the length of a straight line from metacarpale radiale (a radial metacarpal point: a point on the head of the second metacarpal bone projecting most toward the thumb side) to metacarpale ulnare (an ulnar metacarpal point: a point on the head of the fifth metacarpal bone projecting most toward the little finger side) in a state in which a hand (fingers and a palm) is stretched, and the second through fifth fingers are arranged closely side by side, and the thumb is abducted, which is measured from the dorsal side of the hand while the palm is placed on a desk." Therefore, it is desirable that the grasp units 16, 17 are formed in such a manner that the lengths of the holes in the vertical direction are in the range of ±10 mm and desirably about ±5 mm of 95 mm, which is the maximum value, as the center. Hereinafter, the size of a hand shown in "AIST Data on Size of Hand of Japanese" (https://www.dh.aist.go.jp/database/hand/data/list.html) will be used as the size of a hand.

Further, the mean of thumb lengths of males is 60.8 mm. Therefore, it is desirable that lengths from center axes of connection units 16B, 17B of the grasp units 16, 17 to edges on the sides of the monitor 15 are in the range of ±10 mm and desirably about ±5 mm of 30 mm, which is about ½ of the thumb length, as the center, to operate the surface of the touch-panel-type monitor 15 while the grasp units 16, 17 are being held by hand.

Further, the mean of hand lengths from wrist creases of males is 183 mm, and the mean of palm lengths of middle fingers is 105 mm. The hand length is defined as "the length of a straight line from the wrist crease to the fingertip of the middle finger in a state in which a hand (fingers and a palm) is stretched". Further, the palm length of the middle finger is defined as "a length measured, parallel to the longitudinal axis of the hand, from the center of the wrist crease to a crease or creases at the base of the middle finger in a state in which a hand (fingers and a palm) is stretched, and the thumb is abducted, and the other four fingers are arranged closely side by side. In the case that there are plural creases at the base of the middle finger, the most proximal one of the creases (closest to the body) is used for measurement." Therefore, it is desirable that the sizes, such as diameters, of the connection units 16B, 17B of the grasp units 16, 17 are in the range of ±10 mm and desirably about ±5 mm of 40 mm, which is ½ of a difference between the mean of hand lengths and the mean of palm lengths of the middle finger, as the center.

Further, in the present embodiment, the input unit 24 is a touch-panel-type input unit integrated with the monitor 15. An operator performs various kinds of setting for the radiation irradiation apparatus 10 by touching the monitor 15. The operator handles the radiation irradiation apparatus 10 by gripping the grasp units 16, 17 by both hands. Therefore, in the present embodiment, an operation by touching the monitor 15 by the thumb or thumbs is possible. Next, an operation by touching the monitor 15 will be described. Meanwhile, display on the monitor 15 or the like in the following description is performed by the drive control unit 23.

Figure 5:
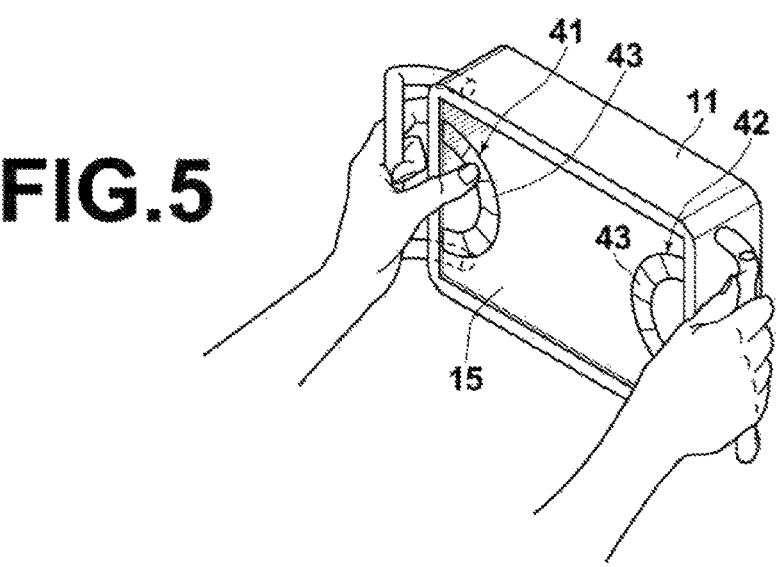
FIG. 5 is a diagram illustrating setting menus displayed on a monitor.

In the case that an operator touches a part of the monitor 15, setting menus 41, 42 of the radiation irradiation apparatus 10 are displayed at left and right edges on the monitor 15, as illustrated in FIG. 5. FIG. 5 illustrates a state in which the monitor 15 is touched by the left thumb. Here, the setting menus 41, 42 may be displayed only at a position at which the monitor 15 has been touched. Alternatively, the setting menus 41, 42 may be displayed in an area around the position at which the monitor 15 has been touched, as the center, or an area around a position in the vicinity of the position at which the monitor 15 has been touched, and which is away to some extent from the position at which the monitor 15 has been touched, as the center.

The setting menus 41, 42 are menus for setting parameters for each unit of the radiation irradiation apparatus 10, or driving the radiation irradiation apparatus 10. Here, drive of the radiation irradiation apparatus 10 is drive of the collimator 14, ON/OFF of the irradiation field lamp 29, an operation of outputting radiation in the case that the radiography button 18 is not provided, and the like.

Each of the setting menus 41, 42 includes plural commands 43, and the plural commands are arranged in arc shape with a position touched by a finger or the vicinity of the position, as the center. The plural commands are displayed within a range reachable by a finger from the position touched by a finger. Here, the arrangement of the plural commands 43 is not limited to arc shape. The plural commands 43 may be arranged on the circumference of an ellipse or linearly as long as the plural commands 43 are in the range reachable by a finger or fingers. In the case that the plural commands 43 are arranged linearly, the plural commands 43 may be arranged on a straight line orthogonal to a direction in which the grasp units 16, 17 project, in other words, a vertical direction of the monitor 15. Further, since the setting menus 41, 42 are able to be swiped, the plural commands 43 may be arranged in a horizontal direction of the monitor 15.

The operator selects a desirable command from the setting menus 41, 42 displayed on the monitor 15. In this case, the operator may rotate the setting menus 41, 42 by swiping the setting menus 41, 42, and display, on the monitor 15, a command or commands that are hidden and not visible in an initial state. In this case, the operator may select the desirable command 43 by successive taps. Accordingly, it is possible to prevent wrong selection of a command, and to securely select a desirable command.

Next, processing performed during radiography of subject H to be examined by using the radiation irradiation apparatus 10 according to the present embodiment will be described. In the present embodiment, it is assumed that two operators handle the radiation irradiation apparatus 10 and the radiation detector 30, respectively, and perform pre-radiography operations for positioning the radiation detector 30 toward the back side of subject H to be examined or setting an irradiation field, and perform radiography after the pre-radiography operations are completed. First, the radiation irradiation apparatus 10 is held above subject H to be examined, and photographic image G1 of subject H to be examined is obtained by performing photography on subject H to be examined by the camera 13.

Imaged image G1 is sent to the console 50, and detection of the radiation detector 30 or the like is performed, and various kinds of information obtained by processing are sent to the radiation irradiation apparatus 10. Various kinds of information are displayed on the monitor 15 of the radiation irradiation apparatus 10 in such a manner to be superimposed on the photographic image G1.

Figure 6:
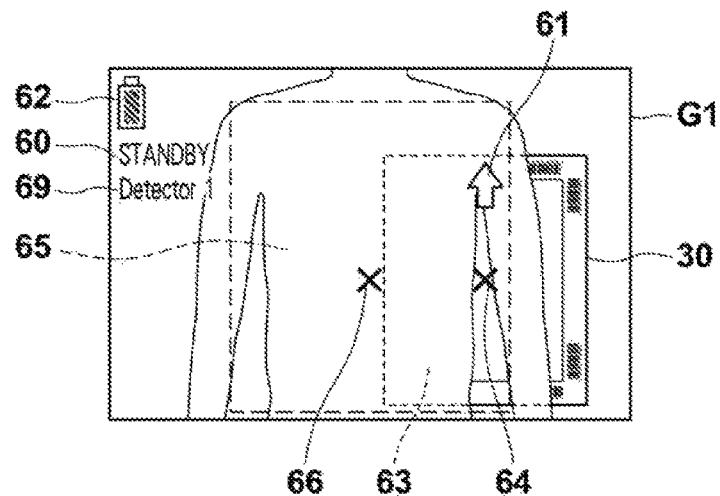
FIG. 6 is a diagram illustrating a photographic image on which various kinds of information are superimposed.

FIG. 6 is a diagram illustrating photographic image G1 on which various kinds of information are superimposed. As illustrated in FIG. 6, a text 60 representing the drive state of the radiation detector 30 ("STANDBY" in this case), an arrow 61 indicating the vertical direction of the radiation detector 30, an icon 62 representing a remaining amount of a battery of the radiation detector 30, a detection area 63 corresponding to a detection area of the radiation detector 30, a center position 64 of the radiation detector 30, an irradiation field area 65, a center position 66 of the irradiation field area 65, and the text 69 of "Detector 1", which is identification information of the radiation detector 30, are displayed by being superimposed on photographic image G1 displayed on the monitor 15. In the irradiation field area 65, the center position 66 of the irradiation field is also displayed. It is desirable that the detection area 63 and the irradiation field area 65 are displayed in such a manner that they are distinguishable from each other. For example, it is desirable that the color of the detection area 63 and the color of the irradiation field area 65 differ from each other. Colors may be specified by an instruction from the console 50.

In the console 50, it is desirable that the color of the clothes of subject H to be examined is detected in photographic image G1, and the colors of the detection area 63 and the irradiation field area 65 are specified so that the colors differ from the color of the clothes. Accordingly, it is possible to prevent the detection area 63 and the irradiation field area 65 superimposed on photographic image G1 from becoming undistinguishable from the clothes of subject H to be examined.

The operators of the radiation irradiation apparatus 10 and the radiation detector 30 cooperate to perform pre-radiography operations. Specifically, the operator of the radiation detector 30 moves the radiation detector 30 to an appropriate position toward the back side of subject H to be examined, and the operator of the radiation irradiation apparatus 10 checks whether the radiation detector 30 has moved to the appropriate position while observing an image displayed on the monitor 15. The position of the radiation irradiation apparatus 10 is moved, if necessary. It is possible to match the center position 66 of the irradiation field area 65 and the center position 64 of the detection area 63 to each other by this operation, as illustrated in FIG. 7.

Further, in the console 50, judgment is made as to whether the center position of the radiation detector 30 has been matched to the center position 66 of the irradiation field area 65. If the center position of the radiation detector 30 has been matched to the center position 66 of the irradiation field area 65, information representing the matched state may be sent to the radiation irradiation apparatus 10. In the case that the radiation irradiation apparatus 10 receives the information representing the matched state, the radiation irradiation apparatus 10 displays information that center positions are matched, for example, such as the text of "Center positions are matched" or a mark representing that the center positions are matched, on the monitor 15. In FIG. 7, the state in which the center positions are matched is represented by a star mark 68. Instead of display on the monitor 15, any method, such as output by voice or a blink of the monitor 15, may be used as long as it is possible to notify the operator or operators that the center position of the radiation detector 30 has been matched to the center position 66 of the irradiation field area 65.

Figure 7:
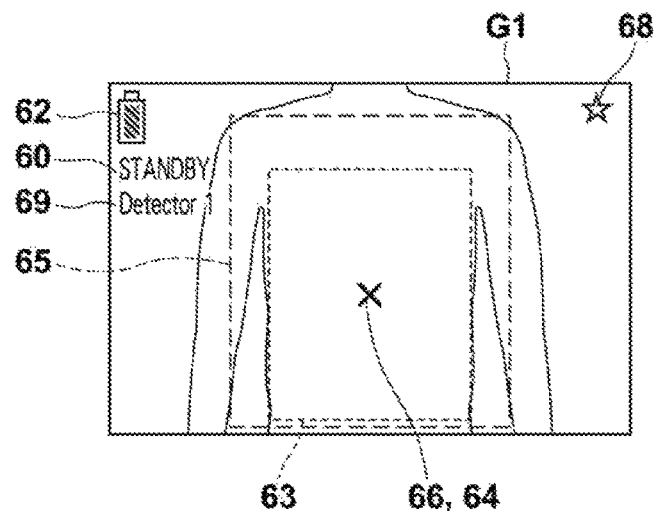
FIG. 7 is a diagram illustrating a state in which a center position of an irradiation field area and a center position of a detection area are matched to each other.
Figure 8:
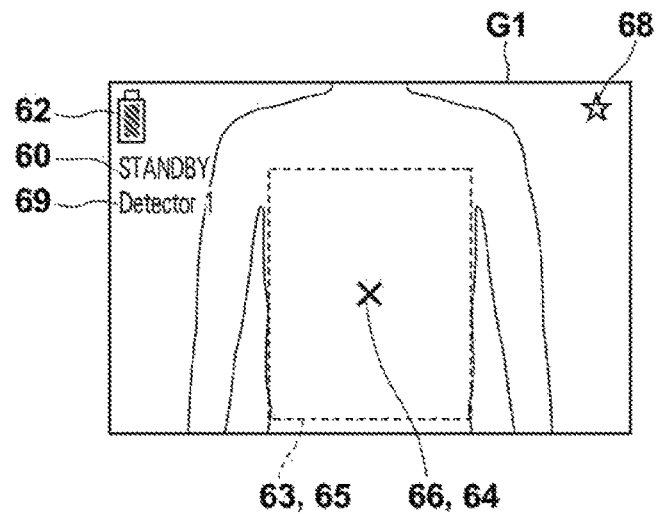
FIG. 8 is a diagram illustrating a state in which the irradiation field area and the detection area are matched to each other.

In the state illustrated in FIG. 7, the size of the irradiation field area 65 is larger than that of the detection area 63. Therefore, it is impossible to generate an image from radiation that has passed through subject H to be examined, but with which the radiation detector 30 has not been irradiated, and such radiation is not utilized. Further, irradiation of subject H to be examined with such radiation that will not be utilized increases the radiation exposure dose of subject H to be examined. Therefore, the operator of the radiation irradiation apparatus 10 gives an area matching instruction to match the irradiation field area 65 and the detection area 63 to each other by using the input unit 24. The area matching instruction is an instruction for matching the irradiation field area 65 displayed on the monitor 15 and the detection area 63 to each other, as illustrated in FIG. 8, by an operation performed on the irradiation field area 65 by a finger or like of an operator. The collimator control unit 21 may drive the collimator 14 in such a manner to be linked with the area matching instruction. However, if the collimator 14 is driven each time when the instruction for matching the irradiation field area 65 and the detection area 63 to each other is given, the consumption amount of electric power becomes large. Therefore, in the present embodiment, the collimator 14 may be driven by the collimator control unit 21 in the case that the input unit 24 has received an input that the area matching instruction for matching the irradiation field area 65 and the detection area 63 to each other by using the input unit 24 has ended and preparation for radiography has been completed.

In the case that preparation for radiography is completed, the drive control unit 23 detects the motion of the radiation irradiation apparatus 10 by the motion sensor 28, and calculates a motion amount of the radiation irradiation apparatus 10 per unit time. The motion amount of the radiation irradiation apparatus 10 per unit time corresponds to hand shake motion of the operator. The drive control unit 23 judges whether the motion amount per unit time is less than threshold Th1. If this judgment is NO, the drive control unit 23 performs warning display on the monitor 15. Because of the warning display, the operator is able to take measures, such as stably holding the radiation irradiation apparatus 10. Further, in the case that the judgment is NO, the drive control unit 23 controls the radiation source 19 so as not to output radiation even if the radiography button 18 is operated. Alternatively, the operation of the radiography button 18 may be prohibited by locking the radiography button 18 or the like. Further, threshold Th1 may be changed based on a time period of irradiation with radiation included in radiography condition. For example, since an influence of hand shake motion is greater as the time period of irradiation with radiation is longer, threshold Th1 may be lowered, as the time period of irradiation with radiation is longer.

If the above judgment is YES, the operator operates the radiography button 18, and thereby the drive control unit 23 outputs radiation toward subject H to be examined by making the drive control unit 23 drive the radiation source 19. In this case, the drive control unit 23 may display information that radiography is possible on the monitor 15. In the case that the above judgment is NO, and changed to YES after then, the drive control unit 23 stops warning display on the monitor 15, and makes the radiation source 19 drivable by an operation of the radiography button 18. Further, in the case that the operation of the radiography button 18 has been prohibited, the radiography button 18 is made operatable by unlocking the radiography button 18 or the like. Accordingly, subject H to be examined is irradiated with radiation, and the radiation detector 30 detects radiation that has passed through subject H to be examined, and radiographic image G2 is obtained. Obtained radiographic image G2 is sent to the console 50, and image processing for improving the image qualities of radiographic image G2 is performed, and radiographic image G2 is sent to the radiation irradiation apparatus 10. In the radiation irradiation apparatus 10, it is possible to check whether radiography has been successful by displaying radiographic image G2 on the monitor 15. In this case, photographic image G1 and radiographic image G2 may be arranged next to each other and displayed. Alternatively, radiographic image G2 may be superimposed on photographic image G1.

As described above, in the present embodiment, plural grasp units 16, 17 that project in directions different from the first direction, which matches to the irradiation direction of radiation and the photography direction of photographic image G1, and the second direction, which is the display direction of the photographic image G1, and are attached to positions of the housing 11 facing each other are provided. Therefore, in the case that the radiation irradiation apparatus of the present embodiment is handled, if the plural grasp units 16, 17 are held by hands, the hands are not irradiated with radiation. Therefore, it is possible to prevent exposure of the hands to radiation. Further, in the case that photographic image G1 is displayed, observation of photographic image G1 is not disturbed by hands.

Figure 9:
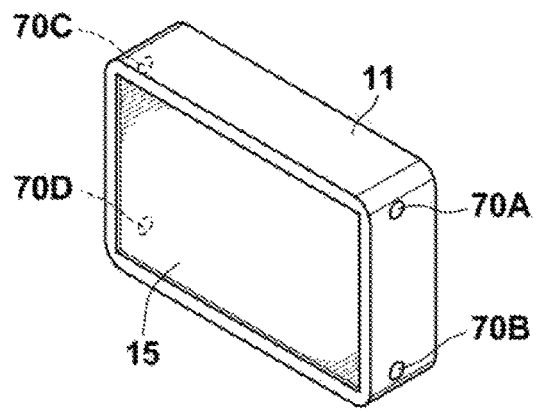
FIG. 9 is a back-side perspective view of the radiation irradiation apparatus from which grasp units are detachable.

In the above embodiment, the grasp unit 16, 17 are fixed to the side surfaces of the housing 11. Alternatively, the grasp units may be made changeable by making them detachable. Next, configuration in which the grasp units are detachable will be described. FIG. 9 is a back-side perspective view of the radiation irradiation apparatus from which grasp units are detachable. As illustrated in FIG. 9, circular insertion holes 70A through 70D for inserting the grasp units, as will be described later, are formed on the side surfaces of the housing 11 in such a manner that two insertion holes are vertically arranged on each of the side surfaces. In the following descriptions, the insertion holes 70A through 70D will be simply represented by insertion holes 70 in some cases.

Figure 10:
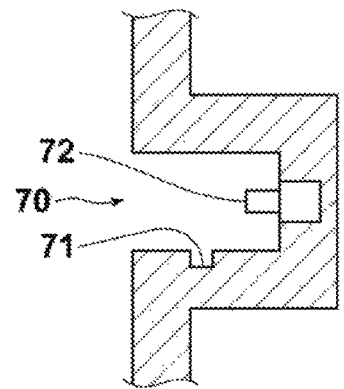
FIG. 10 is a cross section at a center line of an insertion hole.

FIG. 10 is a cross section at a center line of an insertion hole. As illustrated in FIG. 10, a recess 71 is formed on a part of the internal side surface of the insertion hole 70. Further, a switch 72 is attached to the bottom of the insertion hole 70, and the switch 72 is turned on by being pressed down by insertion of a grasp unit, as will be described later. The switch 72 has been energized toward an entrance of the insertion hole 70 by a spring or the like. The switch 72 is off in a state in which the grasp unit has not been inserted. The switch 72 is connected to the drive control unit 23. The drive control unit 23 controls the radiation source 19 so that the radiation source 19 outputs radiation by an operation from the input unit 24 only if the switch 72 is on. Accordingly, it is possible to prevent output of radiation in a state in which the grasp unit is not attached to the housing 11. The switch 72 should be attached to one of the four insertion holes 70. It is desirable that a switch is attached to at least one of the insertion hole 70A or 70B of the two insertion holes and at least one of the insertion hole 70C or 70D of the two insertion holes on the two side surfaces. Further, the diameter of the insertion hole 70 is less than the diameter of the grasp unit. Further, recesses 71 in the upper side insertion holes 70A, 70C are formed on the lower side in FIG. 9, and recesses 71 in the lower side insertion holes 70B, 70D are formed on the upper side in FIG. 9.

Figure 11:
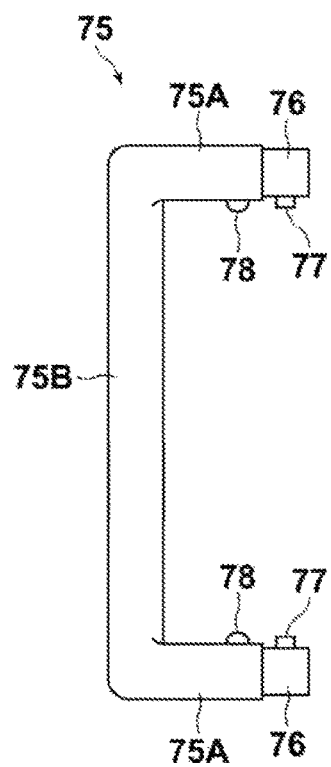
FIG. 11 is a diagram illustrating the structure of a grasp unit that is detachable.

FIG. 11 is a diagram illustrating the structure of a grasp unit that is made detachable. As illustrated in FIG. 11, a detachable grasp unit 75 includes, in a similar manner to the grasp units 16, 17, two projection units 75A which project from an upper part and a lower part of a side surface of the housing 11 toward a lateral direction in the case that being attached to the housing 11, and a connection unit 75B, which connects the two projection units 75A together. An insertion unit 76 the diameter of which fits the insertion hole 70 is formed at a leading end of the projection unit 75A. The insertion unit 76 is structured in a length that is slightly shorter than the depth of the insertion hole 70 and also sufficiently long to turn on the switch 72 in the case that the insertion unit 76 has been inserted in the insertion hole 70. Further, a cylindrical protrusion 77, which has been energized toward the outside of the insertion unit 76 by a spring that is not illustrated, is provided on the insertion unit 76. Further, a button 78 for moving the protrusion 77 toward the inside of the insertion unit 76 is provided in the vicinity of the protrusion 77 in the projection unit 75A. The protrusions 77 are provided at positions facing each other in the two insertion units 76. The protrusion 77 is provided at a position facing the recess 71 of the insertion hole 70 in a state in which the whole insertion unit 76 has been inserted in the insertion hole 70. Here, the insertion hole 70, the insertion unit 76, the protrusion 77 and the button 78 constitute the attachment unit.

In the case that the grasp unit 75, which is configured as described above, is attached to the housing 11, the protrusion 77 is moved toward the inside of the insertion unit 76 against the energizing force of a spring by pressing the button 78 provided on the projection unit 75A of the grasp unit 75. Further, the insertion unit 76 is inserted in the insertion hole 70 of the housing 11 while the button 78 is pressed. In a state in which the whole insertion unit 76 has been inserted in the insertion hole 70, the protrusion 77 has reached the position of the recess 71 of the insertion hole 70. Therefore, in the case that the button 78 is released from a hand, the protrusion 77 projects toward the outside of the insertion unit 76 by the energizing force of the spring. As a result, the protrusion 77 is locked in the recess 71, and the grasp unit 75 becomes undetached from the housing 11 even if the grasp unit 75 is pulled. Further, in this state, the switch 72 is turned on by being pressed by the insertion unit 76. Therefore, the operator is able to irradiate subject H to be examined with radiation by using the radiation irradiation apparatus 10 of the present embodiment by holding the grasp units 75 by hand.

Meanwhile, in the case that the grasp unit 75 is removed, the protrusion 77 is moved toward the inside of the insertion unit 76 against the energizing force of the spring by pressing the button 78 provided on the projection unit 75A of the grasp unit 75. Further, the grasp unit 75 is removable by pulling the grasp unit 75 toward the outside while the button 78 is pressed.

The grasp unit 75 is made changeable by making the grasp unit 75 detachable, as described above. Therefore, grasp units in various sizes and various shapes are usable. For example, in the case that plural kinds of grasp unit 75, in which the lengths of projection units 75A, the sizes, such as diameters, of connection units 75B, the cross-sectional shapes of the connection units 75B and the like are different, are prepared, it is possible to attach, to the housing 11, a grasp unit 75 corresponding to the size of a hand of the operator and a cross-sectional shape easily held by the operator. Therefore, it is possible to make the radiation irradiation apparatus 10 more easily handled. Further, since the grasp units 75 are removable in the case that the radiation irradiation apparatus 10 is not used, it is possible to reduce the space for storing the radiation irradiation apparatus 10.

The structure for attaching the grasp unit to the housing 11 is not limited to the aforementioned structure including the insertion hole 70, the insertion unit 76, the protrusion 77 and the button 78. Any known arbitrary structure may be used.

Figure 12:
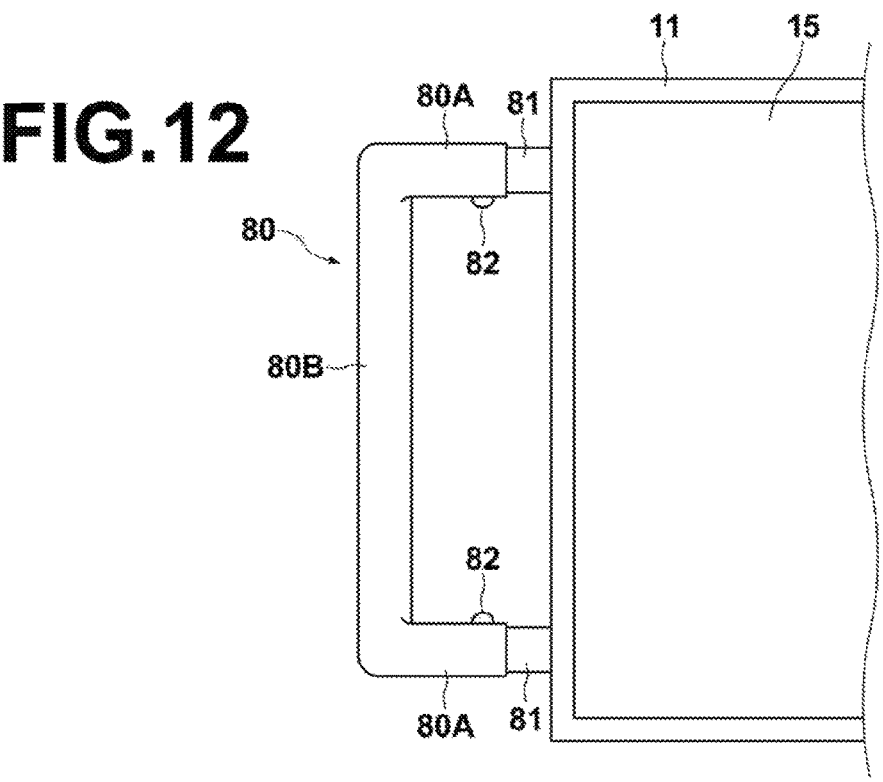
FIG. 12 is a diagram illustrating the structure of a grasp unit the projection amount of which is changeable.

Instead of making the grasp unit detachable, a grasp unit the projection amount of which from the housing 11 is changeable may be used. FIG. 12 is a diagram illustrating the structure of a grasp unit the projection amount of which is changeable. As illustrated in FIG. 12, the grasp unit 80 includes, in a similar manner to the grasp units 16, 17, two projection units 80A which project from an upper part and a lower part of a side surface of the housing 11 toward a lateral direction in the case that being attached to the housing 11, and a connection unit 80B, which connects the two projection units 80A together. Extension units 81 having nest structure are connected to the projection units 80A. Further, stoppers 82 for fixing the extension units 81 to the projection units 80A at desirable positions are provided on the projection units 80A. The operator can release the fixed state of the extension unit 81 with respect to the projection unit 80A by pressing the stopper 82.

In the case that the projection amount of such a grasp unit is to be changed, the operator releases the fixed state of the extension unit 81 with respect to the projection unit 80A by pressing the stopper 82. Then, the operator changes the projection amount of the grasp unit 80 by changing the projection amount of the extension unit 81 from the projection unit 80A while pressing the stopper 82. The operator fixes the extension unit 81 to the projection unit 80A by releasing the stopper 82 from his/her hand when the projection amount has reached a desirable amount. Accordingly, it is possible to change the projection amount of the grasp unit 80 based on the size of the hand of the operator. Therefore, it is possible to make the radiation irradiation apparatus 10 handled more easily.

The structure for changing the projection amount of the projection unit is not limited to the aforementioned structure including the extension unit 81 and the stopper 82, and any known arbitrary structure may be used.

Figure 13:
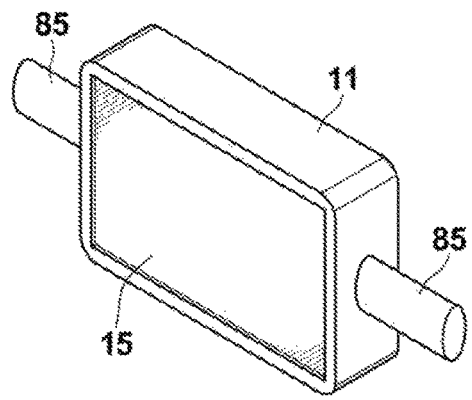
FIG. 13 is a back-side perspective view of the radiation irradiation apparatus in which the grasp units have cylindrical shapes.
Figure 14:
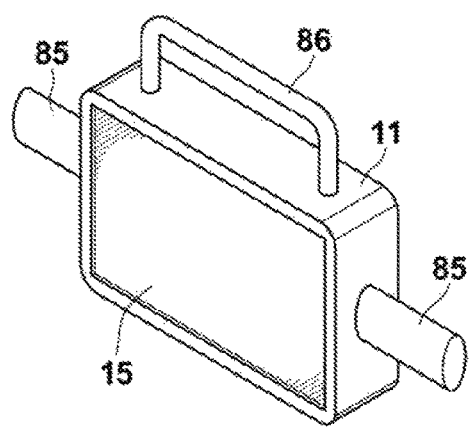
FIG. 14 is a back-side perspective view of the radiation irradiation apparatus in which the grasp units have cylindrical shapes and also a handle is provided.

In the above embodiments, a grasp unit including two projection units and a connection unit connecting them together is used. However, as illustrated in FIG. 13, a grasp unit 85 in cylindrical shape may be used. In this case, the shape of the grasp unit is not limited to the cylindrical shape. The shape may be a prism or an elliptic cylinder. Further, in the case that such a grasp unit 85 in cylindrical shape is used, it is not easy to carry the radiation irradiation apparatus 10 by one hand. Therefore, as illustrated in FIG. 14, a handle 86 may be attached to the top of the housing 11.

Figure 15:
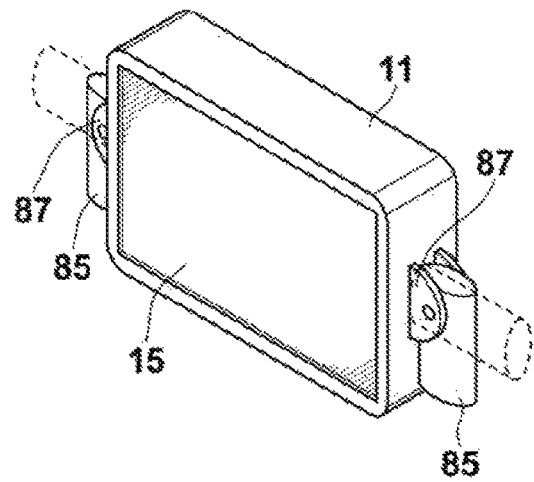
FIG. 15 is a back-side perspective view of the radiation irradiation apparatus in which the cylindrical grasp units are collapsible.

Further, in the case that the grasp unit 85 in cylindrical shape is used, it is desirable that the grasp unit 85 and the housing 11 are connected to each other by a hinge mechanism 87, and the grasp unit 85 is made collapsible, as illustrated in FIG. 15. As a result, it is possible to reduce the space for storing the radiation irradiation apparatus 10.

Further, since the radiation irradiation apparatus 10 according to the present embodiment is a portable-type radiation irradiation apparatus, radiation may be output toward a direction in which subject H to be examined is not present. Therefore, to prevent such output, it is desirable that the radiation source 19 is controlled at the drive control unit 23 so that output of radiation is not possible in a state in which photographic image G1 does not include an object required in radiography by using the radiation detector 30 and the like.

Figure 16:
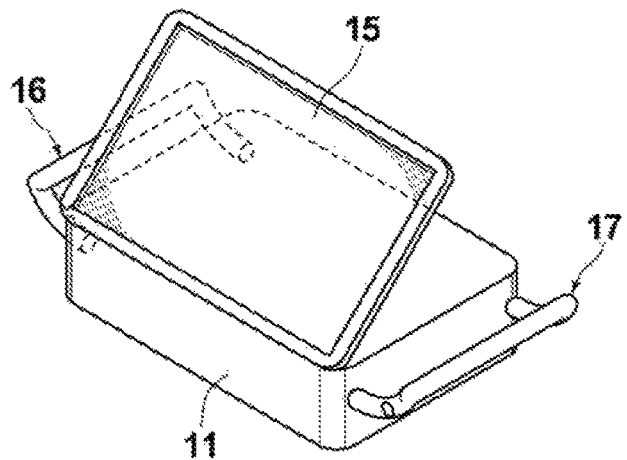
FIG. 16 is a back-side perspective view of the radiation irradiation apparatus in which a monitor is tiltable.

Further, in the above embodiment, it is desirable that the monitor 15 is able to be inclined with respect to the housing 11, as illustrated in FIG. 16. In this case, a drive unit, such as a motor, may be provided, and the monitor 15 may be inclined by driving the drive unit by selection of a command from the touch panel. Alternatively, the monitor 15 may be inclined by hand.

In the above embodiment, the motion of the radiation irradiation apparatus 10 per unit time becomes threshold Th1 or higher during irradiation with radiation in some cases. In such a case, output of radiation is temporarily stopped, and in the case that the motion of the radiation irradiation apparatus 10 per unit time becomes less than threshold Th1, radiation may be output for the remaining radiation irradiation time. In this case, two radiographic images are obtained before stopping output of radiation and after stopping output of radiation. Final radiographic image G2 may be generated by combining the two radiographic images by addition or the like at the console 50.

Further, in the above embodiment, the motion amount of the radiation irradiation apparatus 10 per unit time is calculated by using the motion amount detected by the motion sensor 28. Meanwhile, in the present embodiment, photographic image G1 is obtained at a predetermined frame rate. Therefore, the motion amount of the radiation irradiation apparatus 10 per unit time may be calculated based on two photographic images obtained at different timing of photography and a difference in time of photography of the two photographic images.

Further, in the above embodiment, the camera 13 may be an infrared camera that can measure a temperature distribution in a photography range by using infrared rays. Further, an infrared image representing the distribution of temperature in the photography range may be used as photographic image G1. In this case, photographic image G1 obtained by the camera 13 represents the distribution of temperature on the surface of subject H to be examined and the surface of an object in the vicinity of subject H to be examined. In the case that such a camera 13 that can obtain an infrared image, as photographic image G1, is used, it is possible to identify the position of subject H to be examined in photographic image G1 based on the distribution of temperature represented by photographic image G1 even if subject H to be examined is covered by a sheet or the like in a disaster site or the like.

It is desirable that the camera 13 is switchable between photography with visible light and photography with infrared rays. In the case that the camera 13 switchable between photography with visible light and photography with infrared rays is used, first, photographic image G1 representing a temperature distribution may be obtained by performing photography on subject H to be examined by infrared rays, and the position of an irradiation field may be determined in advance by using photographic image G1 representing the temperature distribution. After then, the camera 13 may be switched to photography with visible light. The detection area of the radiation detector 30 and the irradiation field area may be superimposed on photographic image G1, and displayed, and the position of the radiation detector 30 may be determined by using photographic image G1 in such a manner that detection area of the radiation detector 30 and the irradiation area are matched to each other in a similar manner to the above embodiment. Accordingly, it is possible to obtain radiographic image G2 by matching the irradiation field area and the detection area of the radiation detector 30 even if subject H to be examined is covered by a sheet or the like.

Meanwhile, in the case that photographic image G1 that is an infrared image is displayed on the monitor 15 in this manner, it is possible to recognize an abnormal body temperature of subject H to be examined. Further, radiographic image G2 obtained by radiography and photographic image G1 obtained by photography may be arranged next to each other and displayed on the monitor 15. Accordingly, it is possible to compare the infrared image and radiographic image G2 with each other.

Further, in the above embodiment, the setting menus 41, 42 are displayed by touch on a part of the monitor 15 by an operator. Alternatively, the menus 41, 42 may be displayed by an operation of changing a touched position while a state of touching a part of the monitor 15 is maintained. Alternatively, the setting menus 41, 42 may be displayed by changing pressure during touch. Further, an input to the monitor 15 is not limited to an input by a finger or fingers by an operator, but a touch pen or the like may be used.

Figure 17:
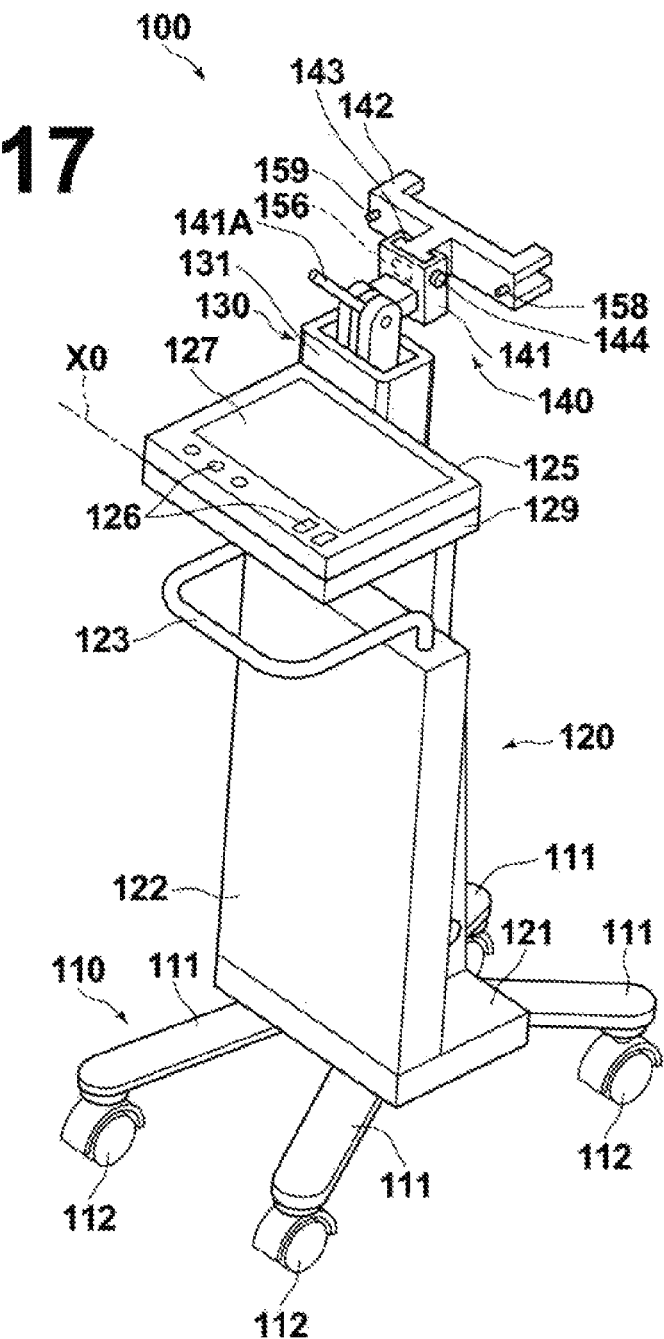
FIG. 17 is a perspective view illustrating the whole shape of a support apparatus.
Figure 18:
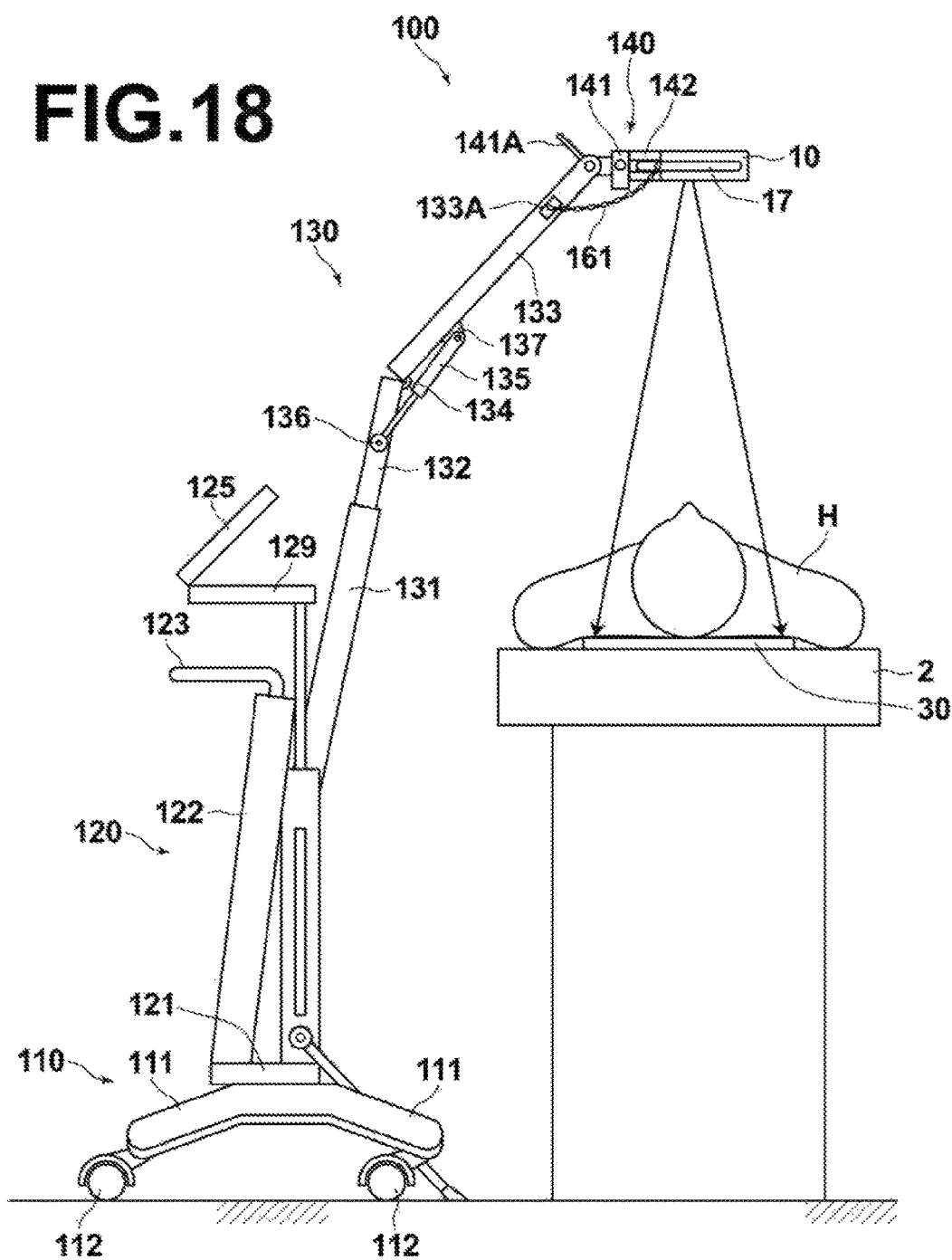
FIG. 18 is a diagram illustrating a state of the support apparatus during use.

Here, the portable-type radiation irradiation apparatus 10 is operatable by an operator while being held by his/her hands. Meanwhile, a support apparatus for supporting the radiation irradiation apparatus 10 has been proposed to prevent hand shake motion during photography and radiography, and further to prevent exposure of hands or the like of an operator to radiation. Specifically, a support apparatus which is made travelable by providing wheel units at lower parts of support legs has been proposed. Therefore, the radiation irradiation apparatus 10 according to the present embodiment may be used by being supported by such a support apparatus. FIG. 17 is a perspective view illustrating the whole shape of the support apparatus, and FIG. 18 is a diagram illustrating a state when the support apparatus is used. A support apparatus 100 includes a leg unit 110 that is made travelable on a surface on which the support apparatus 100 is placed, a main body part 120 held on the leg unit 110, an arm unit 130 connected to the main body part 120, and an attachment mechanism 140 for attaching the radiation irradiation apparatus 10 to a leading end of the arm unit 130.

The leg unit 110 includes four legs 111 and wheel units 112 attached to lower surfaces of leading ends of the legs 111. Further, a brake means, which is not illustrated, is provided for the wheel units 112.

The main body part 120 is configured by housing a control unit and a battery, which are not illustrated, in a housing 122 fixed to a base unit 121. A handle 123 for pushing or pulling the support apparatus 100 is provided at an upper end of the housing 122. Further, an operation unit 125 is attached to an upper part of the base unit 121.

The operation unit 125 includes an input unit 126, such as an operation button for inputting a signal for giving an instruction for various operations of the support apparatus 100 and a switch, a monitor 127 for displaying various kinds of information, and the like. Here, the input unit 126 may be configured by a touch panel in a similar manner to the radiation irradiation apparatus 10 disclosed in the above embodiment. Further, the operation unit 125 is attached in such a manner that the operation unit 125 is rotatable around rotation axis X0 on a support table 129. Accordingly, it is possible to rotate the operation unit 125 with respect to the support table 129, as illustrated in FIG. 18.

The arm unit 130 includes plural members 131, 132 and 133 forming nest structure. The member 132 and the member 133 are connected to each other by a rotary holding mechanism 134. Accordingly, the member 133 is rotationally moved to a direction in which an angle with respect to the member 132 changes. Further, hooks 133A for attaching chains, as will be described later, are attached to both sides of the member 133 in the vicinity of the attachment mechanism 140 in the member 133. Further, an angle sensor, which is not illustrated, is provided in the rotary holding mechanism 134. The angle sensor detects an angle formed by the member 132 and the member 133, and outputs information representing the detected angle to the operation unit 125. Further, the member 132 and the member 133 of the arm unit 130 are connected to each through a gas spring 135.

Here, an end part and the other end part of the gas spring 135 are rotatably held by a holding unit 136 fixed to the member 132, closer to the main body part, and a holding unit 137 fixed to the member 133, closer to the radiation source, respectively. Accordingly, in the case that photography and radiography are performed by arranging, above subject H to be examined, the radiation irradiation apparatus 10 held at the leading end of the member 133, as will be described later, it is possible to prevent unexpected downward inclination of the member 133, and thereby preventing the radiation irradiation apparatus 10 from hitting subject H to be examined. Further, the gas spring 135 includes, in its inside, a lock mechanism for locking a stretched or compressed state by an instruction from the operation unit 125, as will be described later.

An attachment mechanism 140 for attaching the radiation irradiation apparatus 10 of the present embodiment is provided at a leading end of the arm unit 130. The attachment mechanism 140 includes a mount attachment unit 141 that has been swingably attached to the leading end of the arm unit 130, a mount 142 attached to the mount attachment unit 141, and a lock lever 141A that fixes the mount attachment unit 141 at a desirable swing position. The mount attachment unit 141 forms nest structure into which a T-shaped attachment unit 143 of the mount 142 is insertable. The mount 142 the attachment unit 143 of which has been inserted in the mount attachment unit 141 is fixed to the mount attachment unit 141 by screws 144 provided on both sides of the mount attachment unit 141.

Figure 19:
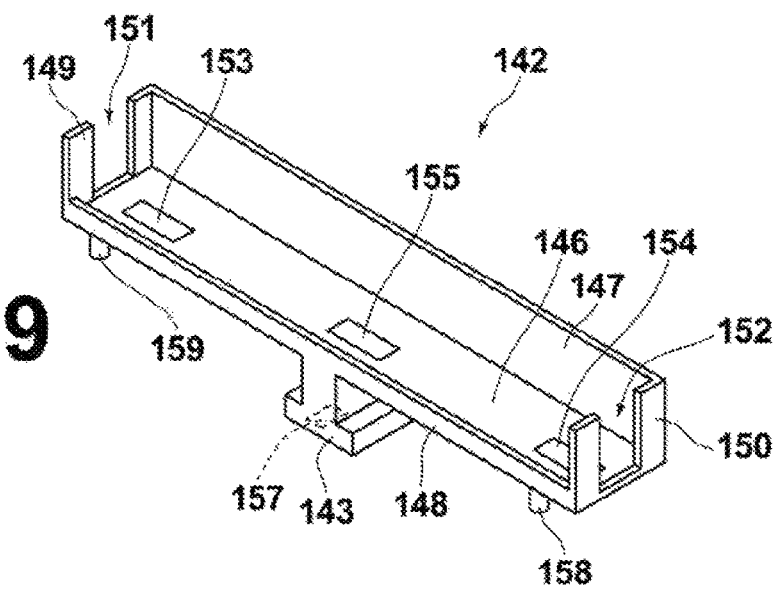
FIG. 19 is a schematic perspective view illustrating the structure of a mount.

FIG. 19 is a schematic perspective view illustrating the structure of a mount. As illustrated in FIG. 19, the mount 142 includes a bottom part 146 having a shape composed of long sides and short sides that conform to the bottom part of the radiation irradiation apparatus 10, a front wall 147 that supports the front side of the radiation irradiation apparatus 10 and is erected on a long side of the bottom part 146, a back wall 148 that supports the back side of the radiation irradiation apparatus 10 and is erected on a long side of the bottom part 146 opposite to the long side on which the front wall 147 is erected, side walls 149, 150 that are erected on two short sides of the bottom part 146, and the aforementioned attachment unit 143 attached to the lower surface of the bottom part 146.

The height of the back wall 148 is lower than that of the front wall 147 so that the monitor 15 is observable in the case that the radiation irradiation apparatus 10 is mounted on the mount 142. Channels 151, 152 are formed on the side walls 149, 150, respectively, so that the side walls 149, 150 do not interfere with the grasp units 16, 17 of the radiation irradiation apparatus 10.

Weight sensors 153, 154 for detecting the weight of the radiation irradiation apparatus 10 mounted on the mount 142 are attached to the upper surface of the bottom part 146. A connector 155 for electrically connecting to the radiation irradiation apparatus 10 mounted on the mount 142 is attached between the weight sensors 153, 154. A connector 157 that is electrically connected to the connector 155, and which will be electrically connected to a connector 156 in the mount attachment unit 141, illustrated in FIG. 17, in the case that the mount 142 is attached to the mount attachment unit 141 is attached to the lower surface of the attachment unit 143. Further, belt attachment units 158, 159 for attaching a belt, as will be described later, are erected in the vicinities of the short sides on the lower surface of the bottom part 146. Meanwhile, a connector (not illustrated) that will be electrically connected to the connector 155 in the case that the radiation irradiation apparatus 10 is mounted on the mount 142 has been attached to the radiation irradiation apparatus 10 that will be attached to the aforementioned attachment mechanism 140.

Figure 20:
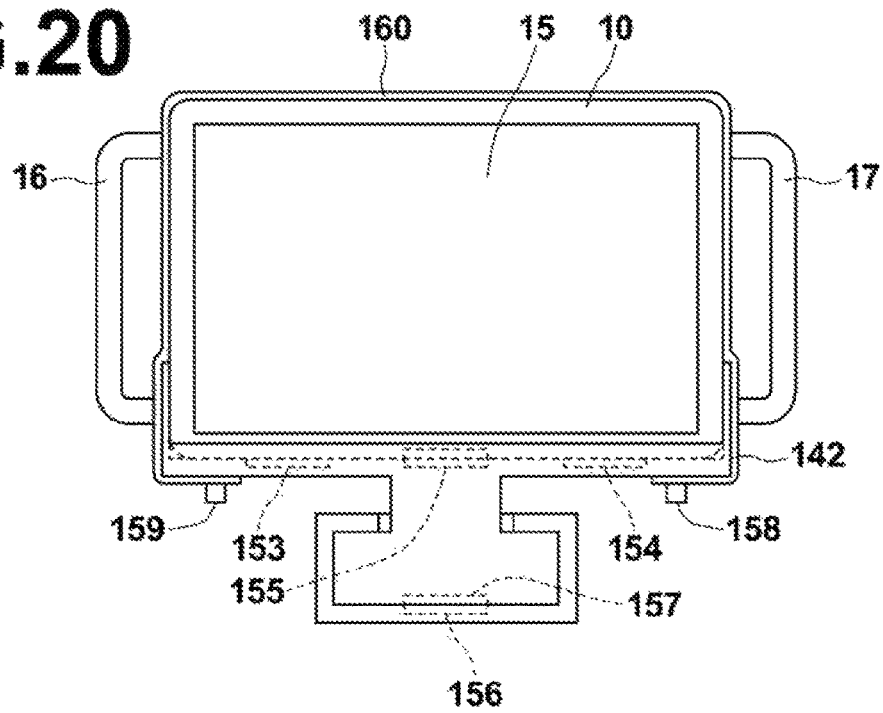
FIG. 20 is a diagram for explaining attachment of the radiation irradiation apparatus.

Next, attachment of the radiation irradiation apparatus 10 to the attachment mechanism 140, which is configured as described above, will be explained. FIG. 20 is a diagram for explaining attachment of the radiation irradiation apparatus 10 to the attachment mechanism 140. FIG. 20 illustrates the back side of the radiation irradiation apparatus 10. Here, it is assumed that the mount 142 has been attached to the mount attachment unit 141. First, the fixed state of the mount attachment unit 141 by the lock lever 141A is released, and the mount 142 is swung so that the upper surface of the bottom part 146 of the mount 142 faces the upside, and the swing of the mount attachment unit 141 is locked. In this state, the radiation irradiation apparatus 10 is mounted on the mount 142, as illustrated in FIG. 20. Accordingly, the connector of the radiation irradiation apparatus 10 and the connector 155 of the mount 142 are electrically connected to each other. Meanwhile, the connector 157 of the mount 142 and the connector 156 of the mount attachment unit 141 are electrically connected to each other. Therefore, the radiation irradiation apparatus 10 mounted on the mount 142 becomes operatable by the operation unit 125.

Meanwhile, in the case that the radiation irradiation apparatus 10 has been mounted on the mount 142, the weight of the radiation irradiation apparatus 10 is measured by the weight sensors 153, 154. The weight sensors 153, 154 are pressure sensitive sensors, and detect the weight of the radiation irradiation apparatus 10 in the case that the radiation irradiation apparatus 10 is placed on the upper surfaces of the weight sensors 153, 154. The detected weight is input to the operation unit 125. Here, in the case that the arm unit 130 to which the radiation irradiation apparatus 10 has been attached is extended, and the member 133 is rotationally moved in such a manner that an angle of the member 133 with respect to the member 132 becomes larger, as illustrated in FIG. 18, the radiation irradiation apparatus 10 attached to the arm unit 130 moves in a direction away from the main body part 120 of the support apparatus 100. In this case, if the weight of the radiation irradiation apparatus 10 is heavy, there is a risk that the support apparatus 100 falls down.

Therefore, the operation unit 125 calculates rotation moment that acts on the main body part 120 by the radiation irradiation apparatus based on the weight of the radiation irradiation apparatus 10 detected by the weight sensors 153, 154, the angle between the member 132 and the member 133 detected by the angle sensor of the rotary holding mechanism 134, and the length of the member 133. The operation unit 125 compares the calculated rotation moment with threshold Th2. Threshold Th2 is determined based on moment that the support apparatus 100 can bear without falling down. Further, in the case that the member 133 is rotationally moved with respect to the member 132, and rotation moment calculated based on an angle of the member 133 with respect to the member 132 exceeds threshold Th2, the operation unit 125 locks the stretched or compressed state of the gas spring 135. Accordingly, the member 133 does not rotationally move with respect to the member 132 any more in such a manner that the angle becomes larger any more. Therefore, the rotation moment acting on the support apparatus 100 does not become greater. Hence, it is possible to prevent the support apparatus 100 from falling down. Here, in the case that the stretched or compressed state of the gas spring 135 is locked, it is desirable that the information that the stretched or compressed extension state of the gas spring 135 is locked is displayed on the monitor 15 or notified by voice. Alternatively, a light emitting device, such as an LCD, may be attached to the support apparatus 100, and in the case that the gas spring 135 is locked, the light emitting device may be turned on.

After the weight is detected, a belt 160 is attached to the belt attachment units 158, 159 of the mount 142 in such a manner that the belt 160 is wound around outer edges of the radiation irradiation apparatus 10 so that the radiation irradiation apparatus 10 does not come off from the mount 142. The belt 160 is elastic, and holes for attaching the belt 160 to the belt attachment units 158, 159 are formed at both ends of the belt 160. Accordingly, the radiation irradiation apparatus 10 is securely fixed to the mount 142. Further, to ensure security, ends of chains 161 may be attached to the grasp units 16, 17 of the radiation irradiation apparatus 10, and the other ends of the chains 161 may be fixed to the hooks 133A of the member 133. Accordingly, even if the radiation irradiation apparatus 10 happens to come off from the mount 142, it is possible prevent the radiation irradiation apparatus 10 from dropping on subject H to be examined. Further, the radiation irradiation apparatus 10 may be fixed to the mount 142 by using a fixing tool, such as a screw.

After the radiation irradiation apparatus 10 is attached to the attachment mechanism 140, as described above, photography is performed on subject H to be examined. Since the radiation irradiation apparatus 10 is electrically connected to the operation unit 125, photographic image G1 of subject H to be examined, which has been obtained by the camera 13 in the radiation irradiation apparatus 10, is displayed on a monitor 127 of the operation unit 125. Here, instead of display on the monitor 127, various kinds of display may be performed on the monitor 15 of the radiation irradiation apparatus 10.

Before photography, the operator extends the arm unit 130, and sets the length of the arm unit 130 and the swing position of the radiation irradiation apparatus 10 in such a manner that the radiation irradiation apparatus 10 is positioned right above subject H to be examined. In the case that photography is performed on subject H to be examined by the camera 13 in this state, it is possible to control the drive state of at least one of the radiation irradiation apparatus 10 or the radiation detector 30 based on whether the radiation detector 30 is present in photographic image G1 in a similar manner to the aforementioned embodiment.

Here, the radiation irradiation apparatus 10 may be operated by using the monitor 15 of the radiation irradiation apparatus 10 instead of the operation unit 125 also in the case that the radiation irradiation apparatus 10 is attached to the support apparatus 100. In this case, various kinds of instruction may be input to the radiation irradiation apparatus 10 by using the aforementioned setting menus 41, 42. However, if the radiation irradiation apparatus 10 is attached to the support apparatus 100, the operator does not need to hold the radiation irradiation apparatus 10 by both hands. Therefore, various kinds of input for the radiation irradiation apparatus 10 may be performed by using an interface in place of the setting menus 41, 42. Here, the change of the setting menu in this case may be performed by detecting the motion of the radiation irradiation apparatus 10 by the motion sensor 28. Specifically, in the case that the radiation irradiation apparatus 10 is held by hand, it is impossible to completely stop the motion of the radiation irradiation apparatus 10. Therefore, the motion of the radiation irradiation apparatus 10 is detected by the motion sensor 28. However, in the case that the radiation irradiation apparatus 10 is attached to the support apparatus 100, it is possible to completely stop the motion of the radiation irradiation apparatus 10. Therefore, the motion of the radiation irradiation apparatus 10 is not detected by the motion sensor 28. Hence, a setting menu to be displayed may be changed based on whether a motion has been detected by the motion sensor 28.

Figure 21:
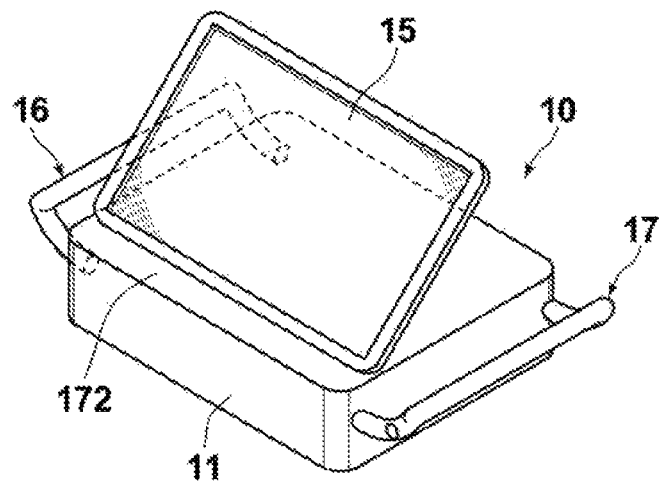
FIG. 21 is a diagram illustrating another example of the radiation irradiation apparatus.

In the case that the apparatus is configured in such a manner that the monitor 15 is inclinable with respect to the housing 11, as illustrated in FIG. 16, if the radiation irradiation apparatus 10 is attached to the mount 142, it becomes impossible to incline the monitor 15 because the back wall 148 of the mount 142 is present. Therefore, the mount 142 without the back wall 148 may be used. Further, as illustrated in FIG. 21, the length of the housing 11 of the radiation irradiation apparatus 10 may be extended in the direction in which the grasp units 16, 17 extend, and an abutment part 172 on which the back wall 148 of the mount 142 abuts may be provided toward the lower side the monitor 15 in the housing 11. Accordingly, it is possible to incline the monitor 15 with respect to the housing 11 in the state in which the radiation irradiation apparatus 10 has been attached to the support apparatus 100. Therefore, in the case that the radiation irradiation apparatus 10 is operated by using the monitor 15, an operation becomes easy.

Figure 22:
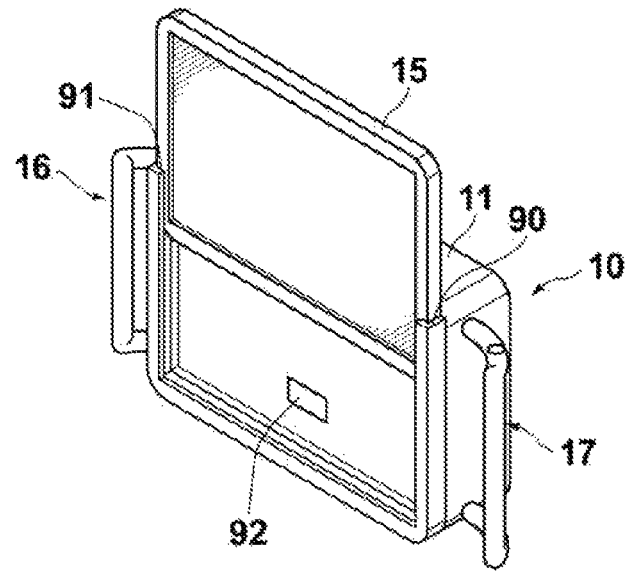
FIG. 22 is a back-side perspective view illustrating a radiation irradiation apparatus from which a monitor is detachable.

Further, the monitor 15 of the radiation irradiation apparatus 10 may be detachable from the housing 11. FIG. 22 is a back-side perspective view illustrating the radiation irradiation apparatus 10 from which the monitor 15 is detachable. As illustrated in FIG. 22, guide grooves 90, 91 for inserting the monitor 15 are formed at side parts on the back side of the housing 11. The monitor 15 is attachable to the housing 11 by inserting the monitor 15, which is made detachable, into the guide grooves 90, 91. Here, a connector 92 for electrically connecting the monitor 15 to the housing 11 in the case that the monitor 15 is attached to the housing 11 has been attached to the back side of the housing 11. Further, a connector has been attached to a position that will correspond to the connector 92 in the case that the monitor 15 is attached to the housing 11. Accordingly, in the case that the monitor 15 is attached to the housing 11, the monitor 15 is driven by a battery in the housing 11. Alternatively, a battery may be mounted on the monitor 15, and the monitor 15 may be able to be driven alone.

Figure 23:
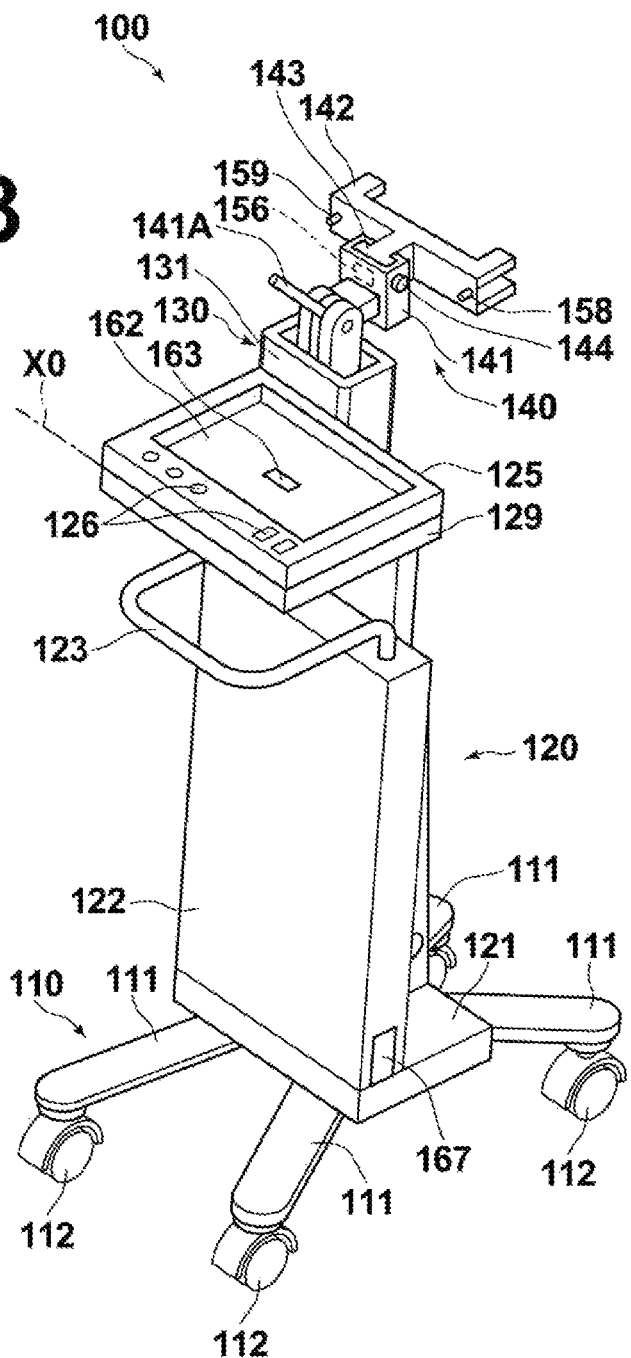
FIG. 23 is a perspective view illustrating the whole shape of another example of a support apparatus.
Figure 24:
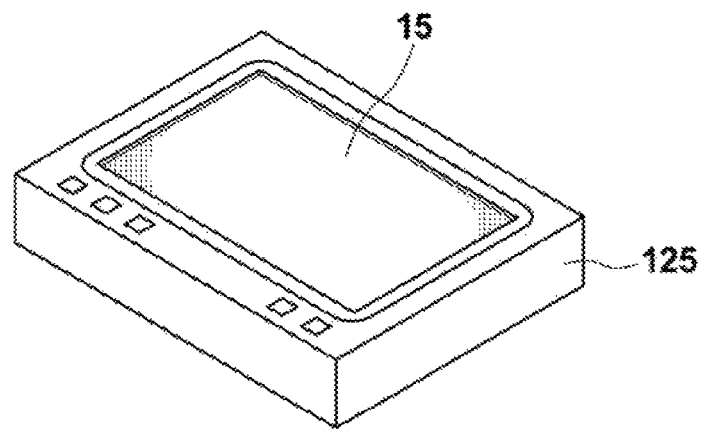
FIG. 24 is a diagram illustrating a state in which a monitor is attached to a monitor attachment unit of an operation unit.

Here, as illustrated in FIG. 23, it is desirable that a monitor attachment unit 162 for attaching the monitor 15 that has been detached from the radiation irradiation apparatus 10 and a connector 163 for electrically connecting to the detached monitor 15 are provided in the operation unit 125 of the support apparatus 100. Accordingly, it is possible to attach the monitor 15 that has been detached from the radiation irradiation apparatus 10 to the monitor attachment unit 162 of the operation unit 125, as illustrated in FIG. 24. In this case, the connector of the monitor 15 and the connector 163 of the operation unit 125 are electrically connected to each other. Accordingly, the monitor 15 functions as an operation unit of the support apparatus 100, and further, as an operation unit of the radiation irradiation apparatus 10 attached to the attachment mechanism 140.

Figure 25:
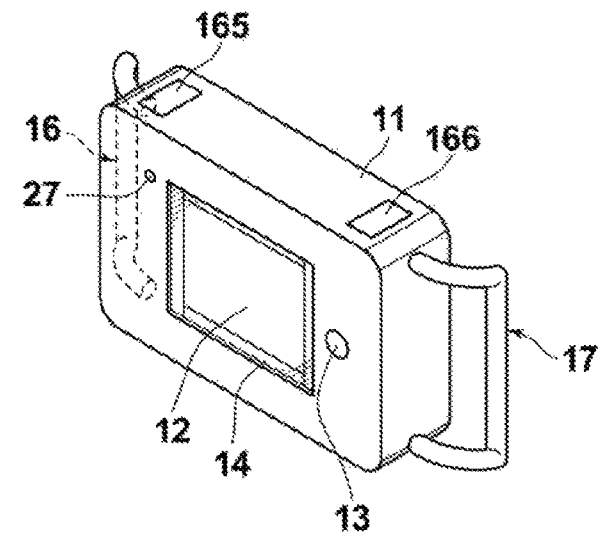
FIG. 25 is a front-side perspective view illustrating a lower surface of a housing of a radiation irradiation apparatus.

Further, in the case that the radiation irradiation apparatus 10 is supported by the support apparatus 100, it is desirable that the weight of the radiation irradiation apparatus 10 is as light as possible. Here, in the case that the radiation irradiation apparatus 10 is attached to the support apparatus 100, the radiation irradiation apparatus 10 and the operation unit 125 are electrically connected to each other. Therefore, it is possible to supply electric power from the battery in the main body part 120 of the support apparatus 100 to the radiation irradiation apparatus 10. Therefore, in the case that the radiation irradiation apparatus 10 is supported by the support apparatus 100, it is desirable that the battery 26 is removed from the radiation irradiation apparatus 10. Here, the battery 26 is attached to the vicinity of each of the grasp units 16, 17 in the housing 11, i.e., two batteries 26 in total are attached by taking the balance of the radiation irradiation apparatus 10 held by hands into consideration. Further, since the batteries 26 are changeable, lids 165, 166 for batteries are provided on the lower surface of the housing 11, as illustrated in FIG. 25.

Therefore, it is desirable that the radiation irradiation apparatus 10 is attached to the attachment mechanism 140 of the support apparatus 100, after the lids 165, 166 of the radiation irradiation apparatus 10 are opened and the batteries 26 are removed. The removed batteries 26 may be stored in a battery storage unit 167 provided in a lower part of the main body part 120 of the support apparatus 100, as illustrated in FIG. 23. The battery storage unit 167 may be provided at an arbitrary position of the main body part 120. However, it is desirable that the battery storage unit 167 is provided in the lower part of the main body part 120 to make the support apparatus 100 less likely to fall down.

Next, actions and effects of the embodiments of the present disclosure will be described.

In the case that plural grasp units project in directions orthogonal to the first direction, it is possible to securely prevent exposure of hands to radiation.

In the case that the display means is a touch-panel-type input means, it is possible to easily perform various kinds of input for the apparatus while the grasp units are held by hand.

In the case that the setting menu or menus are displayed at a touch position on the input means or in the vicinity of the touch position, it is possible to easily operate the setting menu or menus by a finger or fingers.

In the case that a setting menu includes plural commands, it is possible to select a command by moving only a finger by arranging and displaying the plural commands at the touch position or in the vicinity of the touch position.

In the case that selection of a command is received by successive taps, it is possible to securely select a desirable command by preventing wrong selection of a command.

In the case that output of radiation from the radiation source is permitted if the motion amount of the radiation source per unit time has become less than a threshold, it is possible to prevent obtainment of a blurred image caused by motion of the radiation source.

In the case that the grasp unit includes two projection units projecting from the housing and a connection unit connecting the two projection units, and a hole is formed by the two projection units, the connection unit and the housing, it is possible to securely grasp the radiation irradiation apparatus of the present disclosure by inserting a hand in the hole.

Further, in the case that the grasp units are inclined or curved toward the second direction, which is a display direction of the photographic image in the display means, it is possible to easily hold the grasp units by hand.

In the case that the grasp units are detachably attached to the housing, it is possible to attach grasp units in different sizes or in the same size but different shapes to the housing. Therefore, it is possible to grasp the radiation irradiation apparatus by using grasp units in easily graspable size and/or shape based on the size of a hand of an operator who uses the radiation irradiation apparatus of the present disclosure. As a result, it is possible to make the apparatus more easily handled. Further, since the grasp units are removable when the radiation irradiation apparatus of the present disclosure is not used, it is possible to reduce the space for storing the radiation irradiation apparatus.

In the case that output of radiation from the radiation source is permitted only if the grasp units are attached to the housing, it is possible to prevent exposure of hands to radiation caused by output of radiation from the radiation source while a part other than the grasp units is being held.

In the case that the projection amounts of the grasp units are changeable, it is possible to change the projection amounts to a size based on the size of a hand of an operator who uses the radiation irradiation apparatus of the present disclosure so that the grasp units are easily grasped.

In the case that the display means is detachable from the housing, it is possible to reduce the weight of the radiation irradiation apparatus of the present disclosure when the radiation irradiation apparatus of the present disclosure is used by being attached to the support apparatus. Therefore, it is possible to prevent the support apparatus from falling down.

In the case that a setting menu based on the state of use is displayed, it is possible to easily perform setting by using the setting menu appropriate for the state of use of the radiation irradiation apparatus.

What is claimed is:

1. A radiation irradiation apparatus comprising:
    a radiation source that irradiates, with radiation, a subject to be examined;
    a photography unit that obtains a photographic image of the subject to be examined by performing photography on the subject to be examined;
    a display unit that displays the photographic image;
    a housing that houses the radiation source, the photography unit and the display unit with a display direction of the photographic image directed in a second direction opposite to a first direction that is an irradiation direction of the radiation and a photography direction of the photographic image; and
    a plurality of grasp units that project in directions different from the first and second directions and are attached to positions of the housing facing each other.

2. The radiation irradiation apparatus, as defined in claim 1, wherein the plurality of grasp units project in directions orthogonal to the first direction.

3. The radiation irradiation apparatus, as defined in claim 1, wherein the display unit comprises a touch-panel-type input unit.

4. The radiation irradiation apparatus, as defined in claim 3, wherein the display unit displays a setting menu based on a state of touch on the input unit.

5. The radiation irradiation apparatus, as defined in claim 4, wherein the display unit displays the setting menu at a touch position on the input unit or in the vicinity of the touch position.

6. The radiation irradiation apparatus, as defined in claim 4, wherein the setting menu includes a plurality of commands, and the display unit arranges and displays the plurality of commands at the touch position or in the vicinity of the touch position.

7. The radiation irradiation apparatus, as defined in claim 6, wherein the input unit receives, by successive taps on a command, selection of the command successively tapped.

8. The radiation irradiation apparatus, as defined in claim 1, further comprising:
    a motion amount detection unit that detects a motion amount of the radiation source per unit time; and
    a radiography permission unit that permits output of the radiation from the radiation source in the case that the motion amount has become less than a threshold.

9. The radiation irradiation apparatus, as defined in claim 1, wherein the grasp unit includes two projection units projecting from the housing and a connection unit connecting the two projection units together, and a hole is formed by the two projection units, the connection unit and the housing.

10. The radiation irradiation apparatus, as defined in claim 1, wherein the grasp unit is inclined or curved toward the second direction from its projection position.

11. The radiation irradiation apparatus, as defined in claim 1, wherein the grasp units are detachably attached to the housing.

12. The radiation irradiation apparatus, as defined in claim 11, further comprising:
    an output permission unit that permits output of the radiation from the radiation source only if the grasp units are attached to the housing.

13. The radiation irradiation apparatus, as defined in claim 11, further comprising:
    attachment units that can attach, to the housing, the grasp units the projection amounts of which from the housing are different.

14. The radiation irradiation apparatus, as defined in claim 1, wherein projection amounts of the grasp units from the housing are changeable.

15. The radiation irradiation apparatus, as defined in claim 1,
    wherein the photographic image is an infrared image, and
    wherein the display unit displays the infrared image and a radiographic image of the subject to be examined.

16. The radiation irradiation apparatus, as defined in claim 1, wherein the display unit is detachable from the housing.

17. The radiation irradiation apparatus, as defined in claim 1, wherein the display unit displays a setting menu based on the state of use.

* * * * *